US008153561B2

(12) United States Patent
Messerschmidt et al.

(10) Patent No.: US 8,153,561 B2
(45) Date of Patent: Apr. 10, 2012

(54) LIMONENE-CONTAINING HERBICIDE COMPOSITIONS, HERBICIDE CONCENTRATE FORMULATIONS AND METHODS FOR MAKING AND USING SAME FOR ORGANIC PRODUCTION

(75) Inventors: Olav Messerschmidt, East Lansing, MI (US); Joseph Jankauskas, Dacula, GA (US)

(73) Assignee: Cutting Edge Formulations, Inc., Buford, GA (US)

( * ) Notice: Subject to any disclaimer, the term of this patent is extended or adjusted under 35 U.S.C. 154(b) by 1489 days.

(21) Appl. No.: 11/556,287

(22) Filed: Nov. 3, 2006

(65) Prior Publication Data

US 2007/0049496 A1 Mar. 1, 2007

Related U.S. Application Data

(63) Continuation-in-part of application No. PCT/US2006/07426, filed on Mar. 2, 2006, which is a continuation-in-part of application No. 11/071,398, filed on Mar. 2, 2005, now abandoned.

(51) Int. Cl.
*A01N 27/00* (2006.01)
(52) U.S. Cl. ....................................... 504/357
(58) Field of Classification Search ................ None
See application file for complete search history.

(56) References Cited

U.S. PATENT DOCUMENTS

| 2,512,044 | A |   | 6/1950 | Swaney et al. |
| 3,397,053 | A |   | 8/1968 | Bordenca et al. |
| 3,564,046 | A |   | 2/1971 | Newhall |
| 3,592,910 | A |   | 7/1971 | Clark et al. |
| 3,960,539 | A |   | 6/1976 | Newhall |
| 4,379,168 | A | * | 4/1983 | Dotolo ................ 514/763 |
| 4,587,123 | A |   | 5/1986 | Price |
| 5,139,562 | A |   | 8/1992 | Vaughn et al. |
| 5,336,428 | A |   | 8/1994 | Kaplan et al. |
| 5,403,587 | A |   | 4/1995 | McCue et al. |
| 5,407,899 | A |   | 4/1995 | Howell |
| 5,741,502 | A |   | 4/1998 | Roberts |
| 5,753,593 | A | * | 5/1998 | Pullen et al. ............ 504/150 |
| 5,834,533 | A |   | 11/1998 | Patel et al. |
| 5,925,182 | A |   | 7/1999 | Patel et al. |
| 5,951,992 | A |   | 9/1999 | Wilkins |
| 5,998,335 | A |   | 12/1999 | Selga et al. |
| 6,010,978 | A |   | 1/2000 | Lauilhe et al. |
| 6,277,389 | B1 |  | 8/2001 | Pullen |
| 6,500,445 | B1 |  | 12/2002 | Pullen |
| 6,582,712 | B2 |  | 6/2003 | Pullen |
| 6,613,728 | B1 |  | 9/2003 | Sirianni et al. |
| 6,759,370 | B1 |  | 7/2004 | Innes |
| 2004/0092606 | A1 | | 5/2004 | McPartland |
| 2004/0248764 | A1 | | 12/2004 | Franklin |

FOREIGN PATENT DOCUMENTS

| DE | 504333 | 7/1930 |
| WO | WO 93/19598 | 10/1993 |
| WO | WO 94/22304 | 10/1994 |
| WO | WO 97/16975 | * 5/1997 |
| WO | WO-00/49865 | * 8/2000 |
| WO | WO 00/49865 | 8/2000 |
| WO | WO 2004/021787 | 3/2004 |
| WO | WO-2004021787 | * 3/2004 |

OTHER PUBLICATIONS

Vaughn et al., Votatile Monoterpenes as Potential Parent Structures for New Herbicides, Weed Science, vol. 41, pp. 114-119, 1993.*
Journal of Chemical Ecology (1989), 15(5), pp. 1567-1577, G.B. Williamson et al., Chemical inhibition of fire—prone grasses by fire—sensitive shrub, *Conradina canescens*.
Proc, Montana Acad. Sci., (1982), 41 pp. 51-56, T. Weaver and L. Kish, "Allelopathic potential of terpene secreting (aromatic) plants." Weed Control As a Science, G.C. Klingman, John Wiley and Sons, Inc., USA, Sep. 1961 chapter 14 "Other Organic Herbicides" pp. 208-225, in particular pp. 208-218.
Derwent abstract Accession No. 90-284353, EP 388164, (Du Pont De Nemours Co.) Sep. 19, 1990.
Derwent Abstract Accession No. 87-286557, (Shell Int. Res. Miy BV), Oct. 14, 1987.
Derwent Abstract Accession No. 88-216573, JP A 63-152303, (Mitsubishi Petroch KK) Jun. 24, 1988.
Derwent Abstract Accession No. 88-231637, JP A 63-165301, (Shell Kagaku KK) Jul. 8, 1988. Proc. Br. Crop. Prot. Conf., 1985, vol. 1, pp. 265-270, J.W. May et al., "SD 95481 a versatile new Herbicide with wide spectrum crop use."
Journal of Essential Oil Research, Nov./Dec. 1993 issue, pp. 651-657, Massimo Maffei, Silvana Scannerini and Marco Mucciarelli, University of Turin Viale, Paraquat on Carvone Biosynthesis in *Mentha*.
Journal of Chemical Ecology 1985, 11(11), pp. 1527-1534, I.S. AlSaadawi et al., Allelopathic effects of *Citrus aurantium* L.II. Isolation, characterization, an Biological Activities of Phytotoxins.
Bulletin of the Torrey Botanical Club, 1964, 91(4) pp. 327-330, W.H. Muller and C.H. Muller, "Volatile growth inhibitors produced by *Salvia* species".

(Continued)

*Primary Examiner* — Alton Pryor
(74) *Attorney, Agent, or Firm* — Woodard, Emhardt, Moriarty, McNett & Henry LLP

(57) ABSTRACT

Provided are methods, kits and compositions suitable for use in organic production for killing, controlling or suppressing a plant by administering to surfaces of the plant a herbicide composition comprising a herbicidally effective limonene component and an emulsifying agent in an aqueous emulsion, wherein the composition has a pH greater than 5. Also provided are methods, kits and compositions for killing, controlling or suppressing a plant, comprising administering to surfaces of the plant a herbicide composition comprising a herbicidally effective limonene component and an emulsifying agent in an aqueous emulsion, wherein the composition includes a wetting agent and an optional oil. Also provided are methods, kits and compositions for killing, controlling or suppressing a plant, comprising administering to surfaces of the plant a herbicide composition comprising a herbicidally effective limonene component, an emulsifying agent and optionally an added oil component in an aqueous emulsion, wherein the composition has a pH greater than 5 and includes a wetting agent. All components of the compositions suitable for use in organic production contain components which are either natural products obtained by non-chemical means and/or are included on the Environmental Protection Agency's List of Inert Ingredients (List 4A and 4B).

49 Claims, 8 Drawing Sheets

OTHER PUBLICATIONS

Derwent Abstract Accession No. 88-119336, WO-A-8802598 (Du Pont De Nemours Co) Apr. 21. 1988.

The Science of Allelopathy, John Wiley and Sons, New York, (1986), chapter 12, pp. 203-218 N.H. Fischer, "The Function of mono and sesquiterpenes as plant germination and growth regulators."

Biologically active natural products: Potential use in agriculture. Americal Chemical Society symposium series (1988) H.G. Cutler Editor, Washington D.C., Chapter 16 "Terpenoids as models for New Agrochemicals" by S.D. Elakovich pp. 250-261.

Derwent Abstract Accession No. 91-152274, (Sanyo Chem Ind Ltd), Apr. 11, 1991.

The Amer. Midland Naturalist, 1970, vol. 83, pp. 254-282, R. del Moral and C.H. Muller "The allelopathic effects of *Eucalyptus camaldulensis*".

EPA R.E.D. Facts, 1994, EPA-738-F-94-030, "Overview of EPA 1994 Review of Limonene".

MM-01 Herbicide Field Trial, 2004, "Modular Masonry".

D-Limonene Product Data Sheet, 2003, Florida Chemical Co., Inc., www.floridachemical.com.

Special Report, Allelopathic Chemicals, 1983, Alan R. Putnam, Michigan State University, "Nature's herbicides in action".

Weed Science, 1993, Steven F. Vaughn and Gayland F. Spencer, pp. 114-119, "Volatile Monoterpenes as Potential Parent Structures for New Herbicides".

Journal of Chemical Ecology, 2000, vol. 26, No. 3, pp. 611-624, Denise Abrahim, Wellington L. Braguini, Ana M. Kelmer-Bracht and Emy L. Ishii-Iwamoto, "Effects of Four Monoterpenes on Germination, Primary Root Growth, and Mitochondrial Respiration of Maize".

American Potato Journal, 1991, vol. 68, pp. 821-831, Steven F. Vaughn and Gayland F. Spencer, "Volatile Monoterpenes Inhibit Potato Tuber Sprouting".

Quaternary Ammonium Compounds, 1966, William F. Newhall and A.P. Pieringer, University of Florida Citrus Experiment Station, "Derivatives of (+)-Limonene: Quaternary Ammonium Compunds That Retard Plant Growth".

Ann. Appl. Biol, 2002, 141:111-116 (printed in Great Britain), H P Singh, Daizy R. Batish, S Kaur, H Ramezani and R K Kohli, Department of Botany, Panjab University, India, "Comparative phytotoxicity of four monoterpenes against Cassia occidentalis".

Agricultural and Food Chemistry, vol. 7, No. 4, 1959, pp. 264-268, Charles F. Krewson, John W. Wood, and Winthrop C. Wolfe, Eastern Regional Research Laboratory, Eastern Utilization Research and Development Division, U.S. Department of Agriculture, and John W. Mitchell and Paul C. Marth, Crops Research Division, U.S. Department of Agriculture, "Plant Growth Regulators: Synthesis and Biological Activity of Some Quaternary Ammonium and Related Compounds That Suppress Plant Growth".

Journal of the Science of Food and Agriculture, 2004, vol. 84, Issue 11, pp. 1319-1326, MA Ibrahim, EJ Oksanen, JK Holopainen, Department of Ecology and Environmental Science, University of Kuopio, "Effects of limonene on the growth and physiology of cabbage and carrot plants".

American Chemical Society, 1988, Chapter 16, pp. 250-261, Stella D. Elakovich, Department of Chemistry, University of Southern Mississippi, "Terpenoids as Models for New Agrochemicals".

Journal of the Weed Science Society of American, 1996, vol. 44, pp. 6-11, Robert L. Zimdahl, "Weed Science".

British Crop Protection Conference, 1985, pp. 265-270, J.W. May, J.R. Goss, Shell Development Company, J.M. Moncorge, Agrishell, M.W. Murph, Shell Research Limited, "A Versatile New Herbicide with Wide Spectrum Crop Use".

Journal of Chemical Ecology, 1989, vol. 15, No. 5, pp. 1567-1577, G. Bruce Williamson, Nikolaus H. Fischer, Donald R. Richardson, and Ana De La Pena, Louisiana State University, "Chemical Inhibition of Fire-Pronce Grasses by Fire-Sensitive Shrub, *Conradina canescens*".

International Journal of Science, 1969, vol. 223, No. 5209, pp. 965-966, William F. Newhall, University of Florida, Correlation of Pseudocholinesterase Inhibition and Plant Growth Retardation by Quaternary Ammonium Derivatives of (+)-Limonene.

Kim H. Haag—Effects of Herbicide Application on Mortality and Dispersive Behavior of the Water Hyacinth Weevils, *Neochetina eichhorniae and Neochetina bruchi*, Environmental Entomology 15(6), 1192-1198 (1986).

\* cited by examiner

LIMONENE-CONTAINING HERBICIDE COMPOSITIONS, HERBICIDE CONCENTRATE FORMULATIONS AND METHODS FOR MAKING AND USING SAME FOR ORGANIC PRODUCTION

The present application is a continuation-in-part application which claims the benefit of PCT application No. PCT/US2006/07426, filed on Mar. 2, 2006, and published in English which is a continuation-in-part of U.S. application Ser. No. 11/071,398, filed on Mar. 2, 2005 now abandoned and also claims the benefit of U.S. application Ser. No. 11/071,398, filed on Mar. 2, 2005.

BACKGROUND

This invention relates to improvements in the field of herbicidal treatment of plants. The invention involves a method of herbicidal treatment of plants whereby unwanted plants and grasses are terminated using a formulation that can be used in organic production and that is highly effective to non-selectively kill plants it contacts. More particularly, the invention relates to "knock-down" herbicide formulations that comprise a herbicidally active limonene component The methods, formulations and kits according to the present invention further involve formulations which can be used for organic production according to the USDA's National Organic Program and can be labeled "For Organic Production" in accordance with rules promulgated by the USDA.

By way of background, limonene is a naturally occurring chemical found in high concentrations in citrus fruits and spices. Limonene, otherwise known as orange limonene or 1-methyl-4-(1-methylethenyl)cyclohexene or 4-isopropenyl-1-methyl cyclohexene, occurs naturally in various ethereal oils, particularly oils of lemon, orange, lime, grapefruit, caraway, dill and bergamot. It has a chemical formula of $C_{10}H_{16}$, a molecular weight of 136.2, and contains 88.1% Carbon and 11.8% Hydrogen by weight. The d-form of limonene is a liquid having a boiling point of 175.5-176 degrees centigrade.

Some limonene is prepared by extraction from plants of the mint family, a large quantity is obtained from citrus oils, which are typically 80-90% limonene, and some is obtained from pine oil. For example, d-limonene can be obtained from steam extraction of citrus peels of orange, lemon, lime, grapefruit and bergamot. Some of the extractions can contain as high as 90% d-limonene; however, to produce technical grades of d-limonene of higher purity, i.e., greater than about 95%, distillation of the oils is required. d-Limonene can also be synthesized chemically. d-Limonene has a pleasant citrus scent and it can be suitably used in any living environment.

In addition to uses as flavor additives in a wide variety of foods and beverages and uses in perfume materials, d-limonene has also been used in household and industrial cleaning products. It is readily available from commercial sources such as Florida Chemical Company, Inc., and is available in three different grades, named untreated/technical grade, food grade and lemon-lime grade. The food grade comprises about 97% d-limonene, the untreated/technical grade about 95%, and the lemon-lime grade about 70%, the balance in each case being other terpene hydrocarbons and oxygenated compounds.

Limonene has become a valuable industrial chemical. It finds use as a solvent and cleaning agent (in the manufacture of synthetic pine oil), as an expectorant, as a wetting and dispersing agent, as a monomer in the manufacture of various polymeric resins, as a flavorant in many food products and a precursor in the synthesis of the flavorant carvone, and as a polymerization inhibitor in storage of the tetrafluoroethylene monomer used in the manufacture of polytetrafluoroethylene (PTFE). It is also used in many soaps and perfumes for its lemon-like flavor and odor. In addition, limonene is a registered active ingredient in at least 15 pesticide products used as insecticides, insect repellents, and dog and cat repellents. For example, pesticide products containing limonene are used for flea and tick control on pets, as an insecticide spray, an outdoor dog and cat repellent, a fly repellent tablecloth, a mosquito larvicide, and an insect repellent for use on humans.

Limonene is of relatively low acute toxicity taken orally. The U.S. Food and Drug Administration considers limonene Generally Recognized as Safe (GRAS) as a food additive or flavoring, and as a fragrance additive. The U.S. Environmental Protection Agency has granted limonene an exemption from the requirement of a tolerance when it is used as an inert ingredient in pesticide formulations, and when used as an insect repellent tablecloth. For limonene to be used as an active ingredient in a formulation that can be used in organic production, the limonene needs to be from a natural source and obtained by non-chemical means. A more common way of obtaining this form of limonene is through physical separation from a natural source followed by distillation.

Turning now to consideration of herbicides, a wide range of chemicals are used to control weeds in the agricultural industry and to control unwanted vegetation in the landscaping industry. The aim of herbicides is to prevent weeds and unwanted plants from competing with a desired crop in the case of agricultural uses, or competing with preferred vegetation in landscaping applications.

At present, there are two main classes of herbicidal chemicals that are used in connection with terrestrial plants, which is the subject of the present invention. In particular, the herbicides are generally separated into those that have a "contact" action upon plants, and those that have a "systemic" action upon plants. Some herbicides have both a contact and systemic action on plants. Other types of herbicides act in other ways, such as, for example as soil sterilants.

Herbicides may either be selective or non-selective. Selective herbicides, for example "Treflan" (trifluralin), may be utilized for the selective destruction of certain types of grass. Non-selective herbicides such as "Roundup" (glyphosate) may be used as a general herbicide for destroying or controlling many different types of plants and grasses.

A large number of herbicides and plant hormones have been developed over the years. In the early days inorganic compounds such as sodium chlorate and sodium arsenite and various borate compounds were used. There were also developed other organic herbicides such as N-phenylcarbamate, "Randox", and other chlorinated phenoxy compounds. In addition, industrial waste products were quite common. Later on, the hormone type weed killers 2,4-D (2,4-dichloro-phenoxyacetic acid) and 2,4,5-T (2,4,5-trichloro-phenoxyacetic acid) were developed, and have become quite common. More complicated organic weed killers and proprietary chemicals such as "Network" or "Roundup" (both glyphosates) have also been developed.

In many cases herbicides have deleterious effects. For example, they may poison beneficial crops, affect other plants or animals, and/or poison the soil. In addition, many herbicidal compositions presently on the market are highly toxic to humans and domestic animals. Most chemical herbicides are dangerous to mankind and are therefore dangerous when accidentally inhaled and/or absorbed into human and animal tissue. Because of the widespread concern of the deleterious side effects of currently available herbicides, and the problems associated with absorption and ingestion into other living matter, there is much concern as to the long-term use of complex and highly dangerous chemicals, especially when they enter into the food chain. Further, the use of such toxic chemicals in production of foods prevents such foods from being marketed as organic products in a majority of countries. In the United States consumer demand for organic products, particularly foods, has resulted in the development of rules regulating the production of organic food by the USDA. A herbicide having low or no toxicity that can be used in the production of organic products and for home use is desirable in view of the growing demand for organic products, the increased shift toward organic food production and the desire to protect our living environment from toxic materials.

There has been developed recently a relatively nontoxic herbicide which has fatty acids as its main constituents. This herbicide has a smothering effect on plants; however its efficacy is limited particularly in controlling perennial weeds. A further disadvantage is that the fatty acids are not readily carried or emulsified within an appropriate carrier fluid or solvent, which lessens its overall effectiveness due to the difficulties encountered in delivering the herbicide to plants.

It has been suggested recently that limonene can be used at a high concentration as a knock-down herbicide. In U.S. Pat. No. 5,998,335 to Selga et al., knock-down herbicidal compositions are described, one of which comprises about 95-96% by weight of d-limonene and about 4-5% of other components. The '335 patent reports that when this composition was applied to vegetation as a fine droplet spray (targeting 60-80% coverage of vegetation), most vegetation showed visible signs of stress (e.g., wilting or browning) within 2 to 24 hours of application of the herbicide. Selga et al. also reported in the '335 patent that an emulsified mixture of 60% d-limonene with water and commercial emulsifier was also tested. When this formulation was applied to vegetation as described above, most vegetation began showing visible signs of stress within 2 to 36 hours.

One disadvantage of the herbicides described by Selga et al. is that such high concentrations and volumes of limonene would be cost prohibitive and cumbersome for spraying large areas. These formulations also present practical challenges associated with effectively atomizing and spraying such oily or highly viscous compositions.

In light of the above, there is a continuing need for natural, safer, cost effective, and environmentally-friendly herbicides having increased efficiency and efficacy that can be formulated to provide a herbicide suitable for use in organic production in compliance with USDA regulations currently in effect. The present invention addresses this need and provides a wide variety of benefits and advantages.

SUMMARY

Embodiments of the methods, kits, and compositions disclosed herein involve herbicidal compositions containing components that allow the herbicidal compositions to qualify for use in organic production under the USDA's National Organic Program. In order for a herbicide to qualify for use in organic production, a herbicide's components must be a natural products obtained by non-chemical means or synthetic components defined under 7 CFR 205.601. A synthetic compound can comply with 7 CFR 205.601 by being included on the Environmental Protection Agency's lists 4A or 4B (Inerts of Minimal Concern).

A first aspect of the present disclosure provides for a method suitable for use in organic production for killing, controlling or suppressing a plant. The method involves providing a liquid herbicidal composition that includes water, a herbicidally active limonene component, and an emulsifying agent and spraying the herbicidal composition onto one or more leaves of a plant. In order to be suitable for use in organic production the limonene component must be obtained by non-chemical means and the emulsifying agent must either be a natural product obtained by non-chemical means or an inert pesticide ingredient contained in the Environmental Protection Agency's List 4A or 4B. For the purposes of this document, the term "Environmental Protection Agency's List 4A or 4B" shall mean the U.S. Environmental Protection Agency List of Inert Pesticide Ingredients (including List A and List B) provided in Appendix A to this application.

A second aspect of the present disclosure provides for a method suitable for use in organic production for the non-selective burn down of plants. The method utilizes a liquid herbicide that includes water, a herbicidally active limonene component obtained from a natural source by non-chemical means, an emulsifying agent and a member selected from the group consisting of a wetting agent, a pH modifier effective to provide a pH greater than 5, an added oil component and a combination thereof. The emulsifying agent and any member selected from the group and included in the liquid herbicide are inert pesticide ingredients contained in the Environmental Protection Agency's List 4A or 4B. The method involves selecting an area having at least one plant growing within the area and spraying the liquid herbicide composition onto the area.

A third aspect of the present disclosure provides for a "ready to use" herbicidal composition for use in organic production that includes water, a herbicidally active limonene component and an emulsifying agent. The limonene utilized in the ready-to-use composition is a natural product obtained by non-chemical means. The emulsifying agent is a natural product obtained by non-chemical means and/or an inert pesticide ingredient contained in the Environmental Protection Agency's List 4A or 4B provided in Appendix A. Such ready-to-use composition qualifies under the USDA's National Organic Program to be used in organic production and to be labeled "for organic production." Preferred embodiments of the ready-to-use herbicide additionally include a member selected from the group consisting of a wetting agent, a pH modifier effective to provide a pH greater than 5, an added oil component and a combination thereof where the member selected and utilized is an inert pesticide ingredient contained in the Environmental Protection Agency's List 4A or 4B.

A fourth aspect of the present disclosure provides for a herbicidal concentrate suitable for use in organic production that is adapted to be diluted with water. The concentrate includes a herbicidally active limonene component and an emulsifying agent. The limonene utilized in the concentrate is a natural product obtained by non-chemical means and the emulsifying agent is a natural products obtained by non-chemical means and/or an inert pesticide ingredients contained in the Environmental Protection Agency's List 4A or 4B provided in Appendix A. Such herbicidal concentrate qualifies under the USDA's National Organic Program to be used in organic production and to be labeled "for organic production." Preferred herbicidal concentrates additionally contain and a member selected from the group consisting of a wetting agent, a pH modifier effective to provide a pH greater than 5, an added oil component and a combination thereof where the member selected and utilized is an inert pesticide ingredient contained in the Environmental Protection Agency's List 4A or 4B.

A fifth aspect of the present disclosure provides for a method for making a herbicide composition suitable for use in organic production by providing the herbicidal concentrate described above and diluting and mixing the concentrate with water.

A sixth aspect of the present disclosure provides for a kit for providing a ready-to-use herbicide composition for indiscriminately killing, controlling or suppressing plants growing in the area and suitable for use in organic production. The kit includes a container having therein a ready-to-use liquid herbicide and instructions, recorded in a medium, for applying the herbicide to a preselected area. The herbicide composition includes water, a herbicidally active limonene component obtained by non-chemical means, an emulsifying agent and a member selected from the group consisting of a pH modifier effective to provide a pH greater than 5, a wetting agent, an added oil component, and a combination thereof. The emulsifying agent, and the member selected are natural products obtained by non-chemical means and/or are inert pesticide ingredients contained in the Environmental Protection Agency's List 4A or 4B. Preferred kits have a label stating "for organic production."

A seventh aspect of the present disclosure provides for a kit for providing a herbicide composition suitable for use in organic production. The kit includes a container having therein a liquid herbicide concentrate and instructions, recorded in a medium, for diluting the concentrate with water to provide a herbicide composition. The liquid herbicide concentrate includes a herbicidally active limonene component obtained by non-chemical means, an emulsifying agent and a member selected from the group consisting of a pH modifier effective to provide a pH greater than 5, a wetting agent, an added oil component, and a combination thereof. The emulsifying agent and the member selected are either natural products and/or are inert pesticide ingredients contained in the Environmental Protection Agency's List 4A or 4B. Preferred kits have a label stating "for organic production."

An eighth aspect of the present disclosure provides for a kit for providing a herbicide composition suitable for use in organic production. The kit includes:

(a) a first container having therein a liquid herbicide concentrate that includes a herbicidally active limonene component obtained by non-chemical means, an emulsifying agent and a member selected from the group consisting of a pH modifier effective to provide a pH greater than 5, a wetting agent, an added oil, and a combination thereof;

(b) a second container having therein an additive formulation including a member selected from the group consisting of a pH modifier effective to provide a pH greater than 5, a wetting agent, and a combination thereof; and (c) instructions, recorded in a medium, for combining and diluting the concentrate and additive formulation with water to provide a herbicide composition. The emulsifying agent, any member selected from the group consisting of a pH modifier effective to provide a pH greater than 5, a wetting agent, an added oil, and any combination thereof are natural products and/or are inert pesticide ingredients contained in the Environmental Protection Agency's List 4A or 4B. Preferred kits have a label stating "for organic production."

A ninth aspect of the present disclosure provides for a kit for providing a herbicide composition suitable for use in organic production. The kit includes:

(a) a first container having therein a liquid herbicide concentrate that includes a herbicidally active limonene component obtained by non-chemical means and an emulsifying agent;

(b) a second container having therein an additive formulation that includes a member selected from the group consisting of a pH modifier effective to provide a pH greater than 5, a wetting agent, an added oil, and a combination thereof; and (c) instructions, recorded in a medium, for combining and diluting the concentrate and additive formulation with water to provide a herbicide composition. The emulsifying agent and the member selected are a natural product obtained by non-chemical means and/or are an inert pesticide ingredient contained in the Environmental Protection Agency's List 4A or 4B. Preferred kits have a label stating "for organic production."

The compositions, methods and kits disclosed herein provide particular advantages to growers involved in organic production. Currently plastic sheeting, mulch and the like are the predominant methods of weed control allowed in organic production under the USDA's National Organic Program. In order for a herbicide to qualify for use in organic production, its components must be a natural product obtained by non-chemical means or a synthetic component defined under 7 CFR 205.601. A synthetic compound can comply with 7 CFR 205.601 by being included on the Environmental Protection Agency's lists 4A or 4B (Inerts of Minimal Concern). 7 CFR 205.601 and EPA's lists 4A and 4B as they exist on the filing date of this application are hereby incorporated by reference in their entirety to identify the inert ingredients which can be selected for use in products intended for organic production. A 2004 listing of inert pesticide ingredients contained in the EPA's latest published list 4A and 4B is included in Appendix A.

Further objects, features, aspects, forms, advantages and benefits shall become apparent from the description and drawings contained herein.

While the actual nature of the invention covered herein can only be determined with reference to the claims appended hereto, certain forms and features, which are characteristic of the preferred embodiments disclosed herein, are described briefly as follows.

DETAILED DESCRIPTION OF THE PREFERRED EMBODIMENTS

Figure 1:
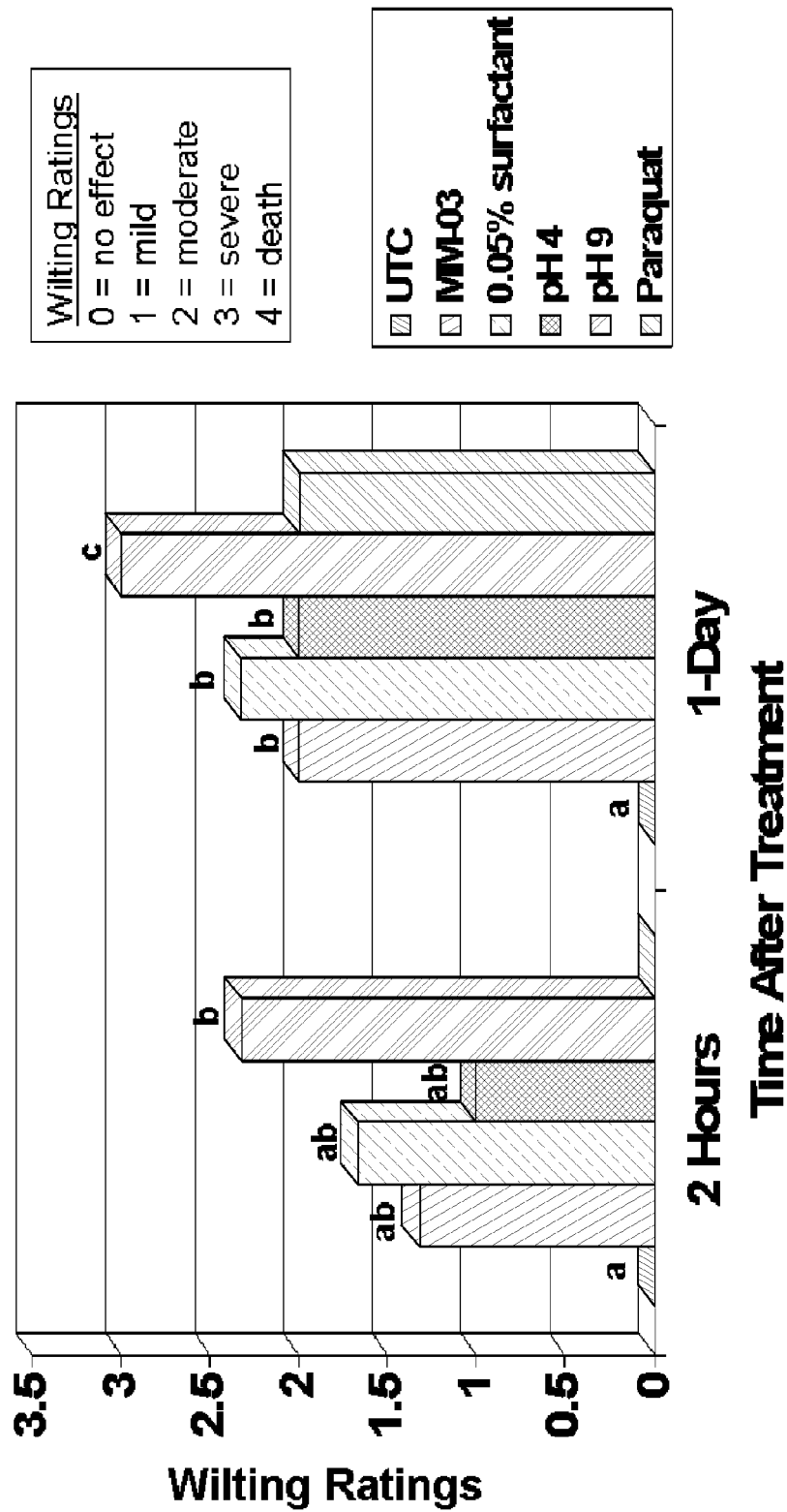
FIG. 1 is a bar graph setting forth the wilting assessment results at 2 and 24 hours from a field study of common grasses and broadleaves in turf conducted in November of 2004. Statistical analysis is by Duncan's MRT (P<<0.05). Treatments with the same letter or letter combination are not significantly different.
Figure 2:
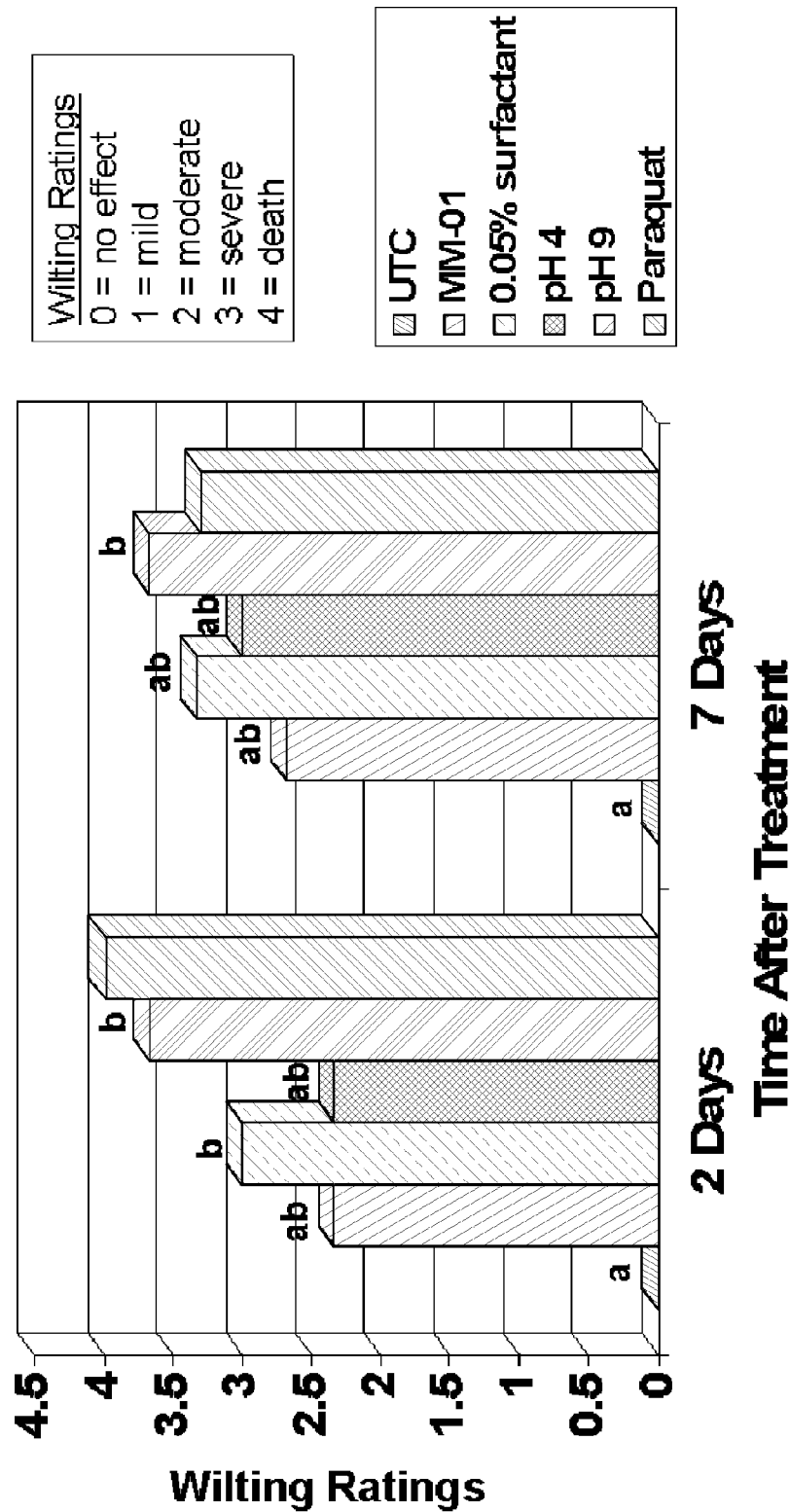
FIG. 2 is a bar graph setting forth the wilting assessment results at 2 and 7 days from a field study of common grasses and broadleaves in turf conducted in November of 2004. Statistical analysis is by Duncan's MRT (P<0.05). Treatments with the same letter or letter combination are not significantly different.
Figure 3:
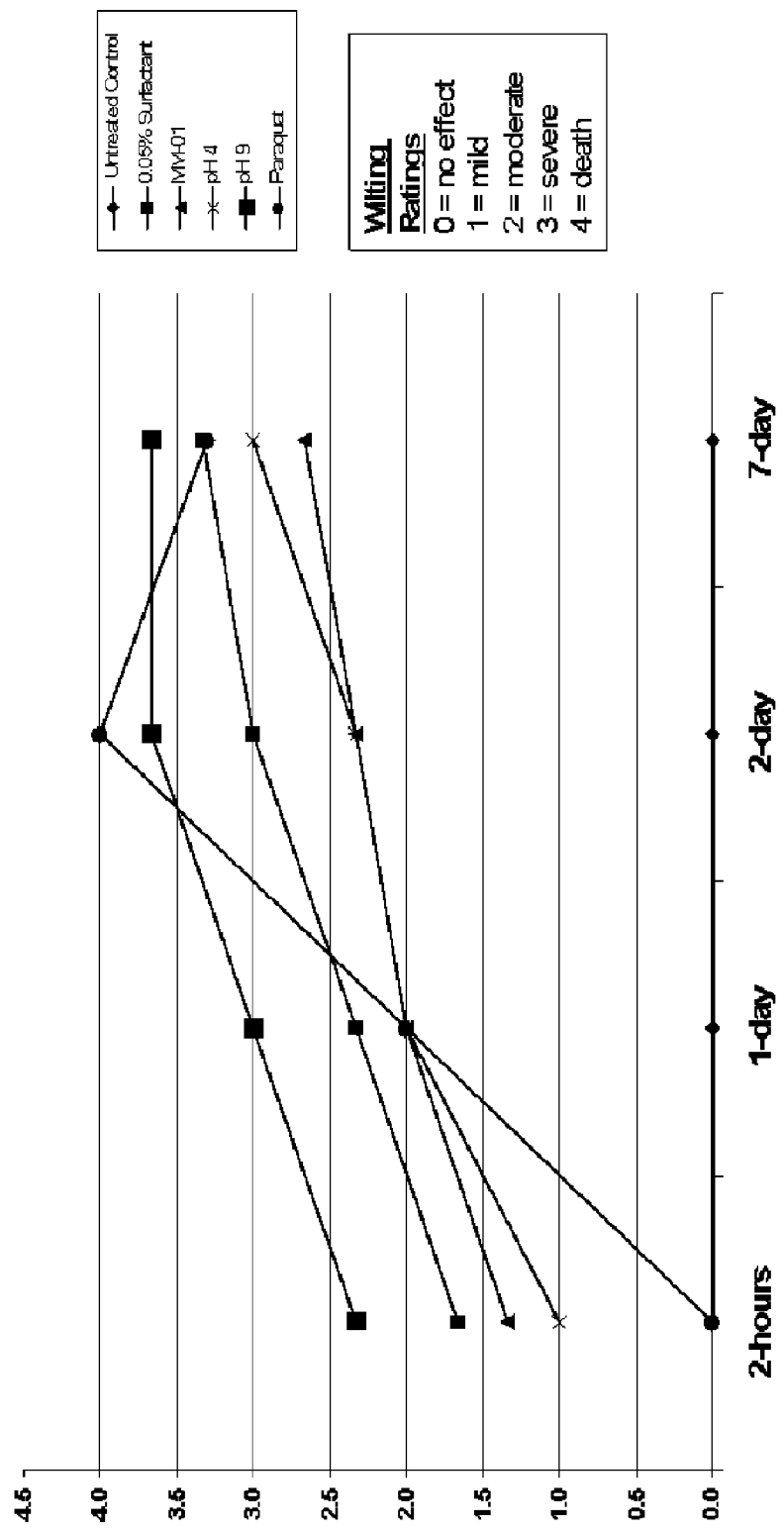
FIG. 3 sets forth a plot of the data presented in FIGS. 1 and 2.
Figure 4:
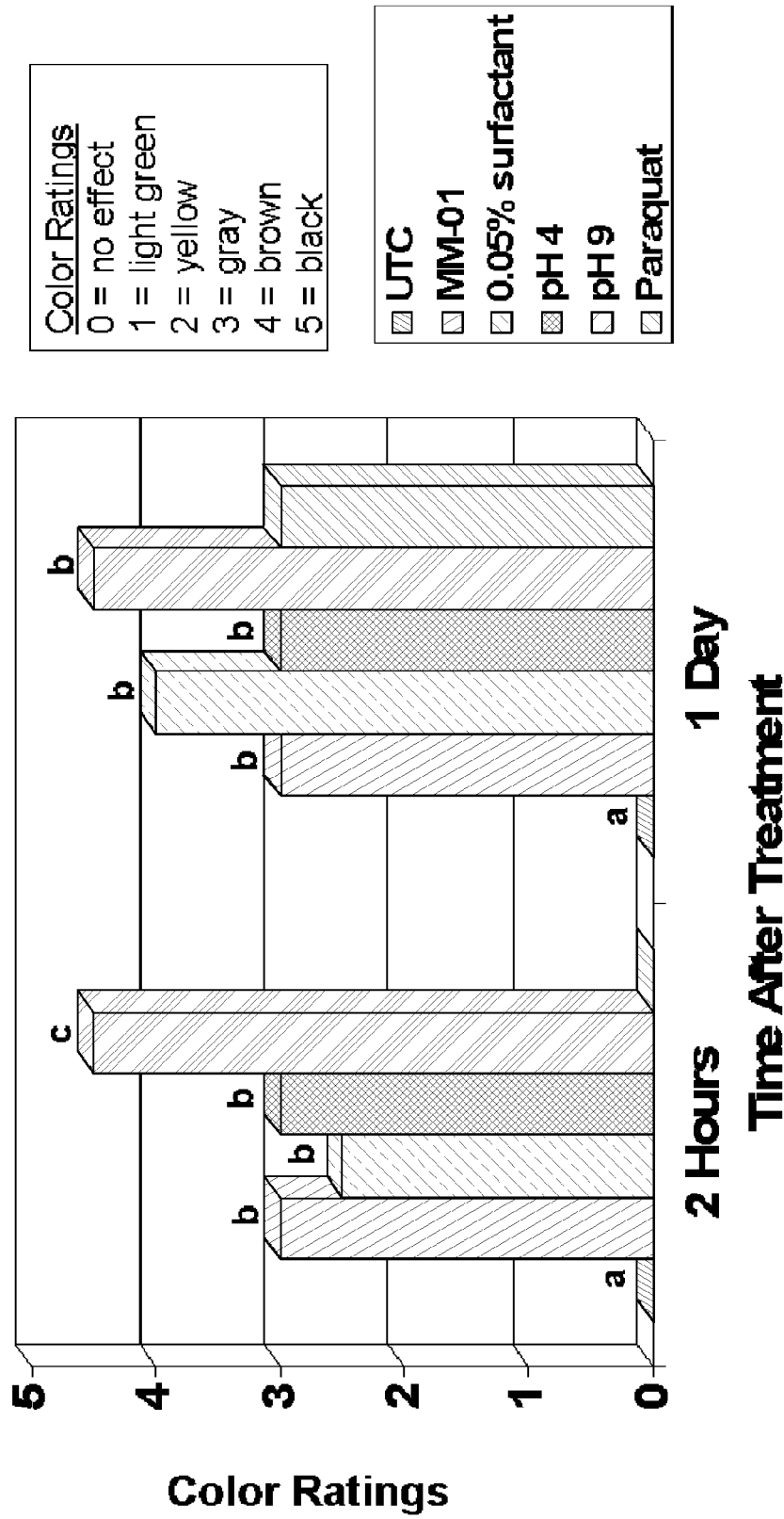
FIG. 4 is a bar graph setting forth the color assessment results at 2 and 24 hours from a field study of common grasses and broadleaves in turf conducted in November of 2004. Statistical analysis is by Duncan's MRT (P_<0.05) Treatments with the same letter or letter combination are not significantly different.
Figure 5:
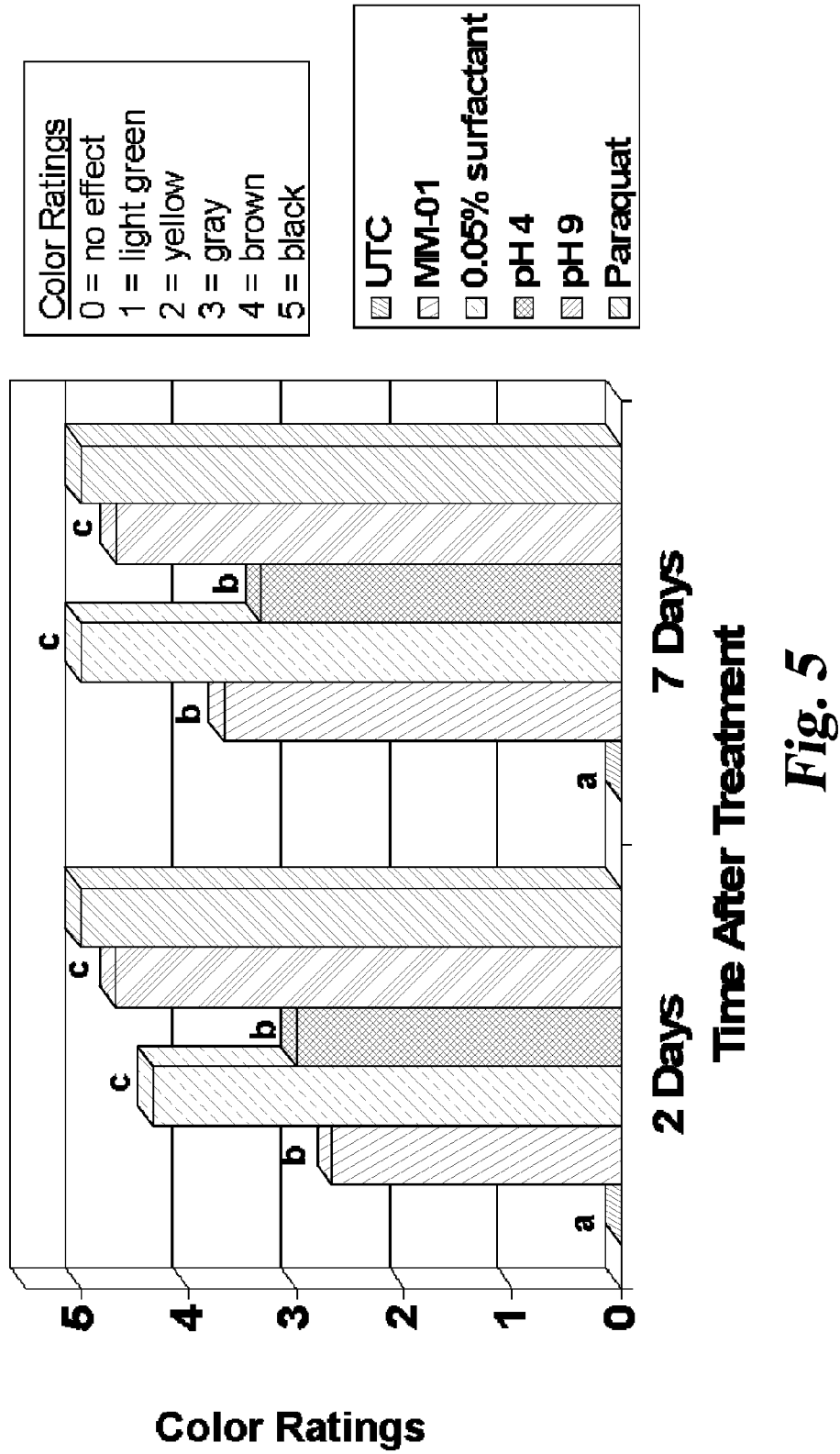
FIG. 5 is a bar graph setting forth the color assessment results at 2 and 7 days from a field study of common grasses and broadleaves in turf conducted in November of 2004. Statistical analysis is by Duncan's MRT (P-0.05). Treatments with the same letter or letter combination are not significantly different.
Figure 6:
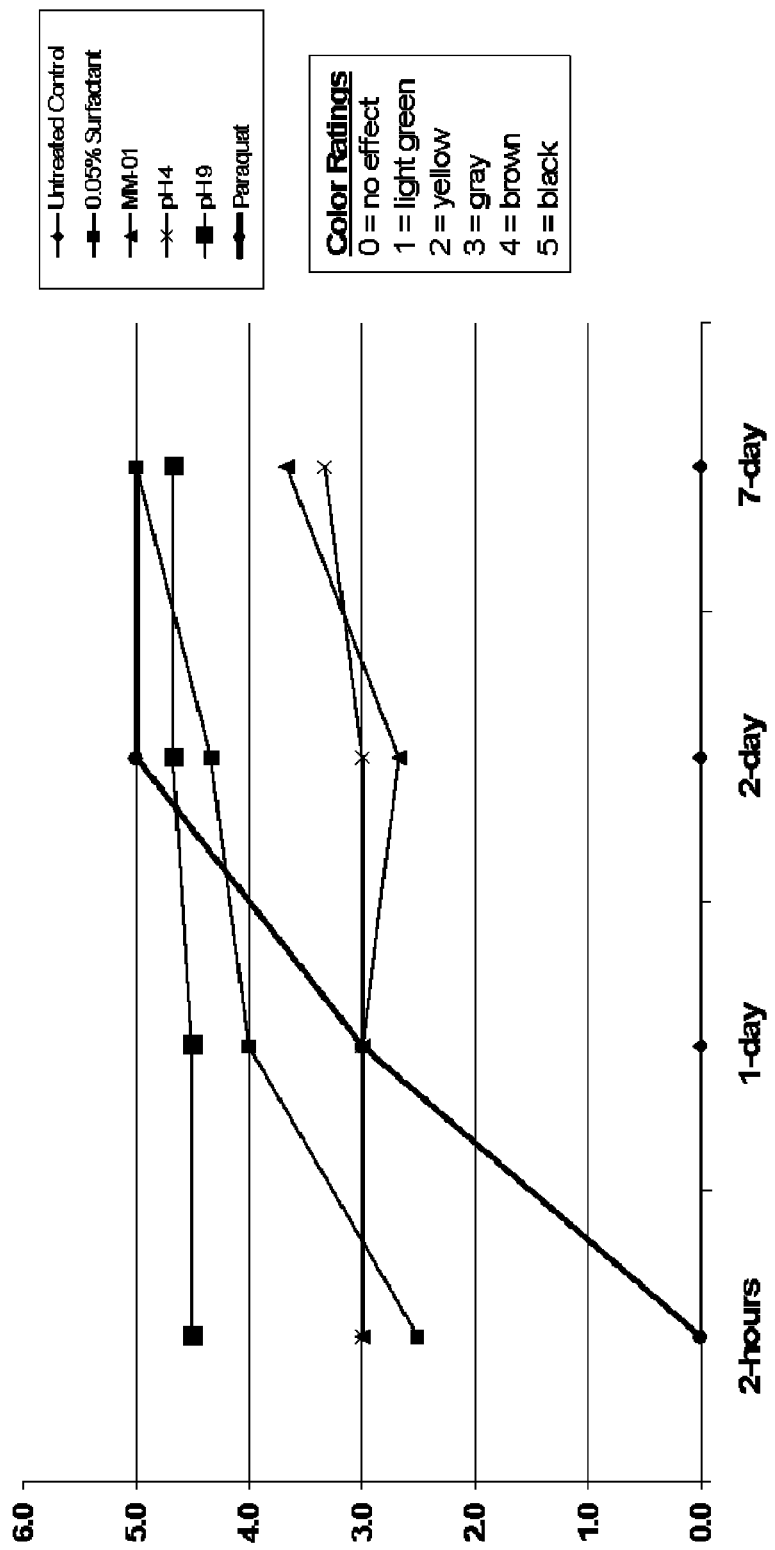
FIG. 6 sets forth a plot of the data presented in FIGS. 4 and 5.

For the purposes of promoting an understanding of the principles of the invention, reference will now be made to the embodiments described herein and specific language will be used to describe the same. It will nevertheless be understood that no limitation of the scope of the invention is thereby intended. Any alterations and further modifications in the described fluids, methods, devices or kits, and any further applications of the principles of the invention as described herein, are contemplated as would normally occur to one skilled in the art to which the invention relates.

It has been discovered that the effectiveness of limonene compositions as non-selective, "burn down" herbicides can be significantly improved by increasing the pH of the composition to a pH of greater than 5, by including a wetting agent in the composition, or both. Accordingly, this invention provides in one embodiment a method of killing, controlling or suppressing a plant by administering to surfaces of the plant a herbicide composition comprising a herbicidally effective limonene component and an emulsifying agent in an aqueous emulsion, wherein the composition has a pH greater than 5. In another embodiment, the invention provides a method of killing, controlling or suppressing a plant by administering to surfaces of the plant a herbicide composition comprising a herbicidally effective limonene component and an emulsifying agent in an aqueous emulsion, wherein the composition includes a wetting agent. In yet another embodiment of the invention, there is provided a method of killing, controlling or suppressing a plant by administering to surfaces of the plant a herbicide composition comprising a herbicidally effective limonene component and an emulsifying agent in an aqueous emulsion, wherein the composition has a pH greater than 5 and includes a wetting agent.

It has further been discovered that the methods, formulations and kits of this present invention can involve herbicide formulations that qualify for use in organic production under the USDA's National Organic Program and qualify to be so labeled.

Additionally, it has been discovered that the addition of increased amounts of an added oil component further enhances the performance of the herbicide. Preferred herbicidal concentrates contain from about 2 weight percent to about 20 weight percent of an added oil component that includes castor oil, cottonseed oil, soybean oil, sunflower oil, pine oil and coconut oil or a combination thereof. Suitable added oil components further include ethoxylated oil derivatives. More preferred embodiments of the herbicide concentrate contains from about 4 weight percent to about 12 weight percent of the added oil component. Provided the added oil component is included in the Environmental Protection Agency's List 4B, it can be incorporated into a herbicide used for organic production under the USDA's Organic Program (7 CFR 205.601) regardless of whether it is a natural product or obtained by chemical means and considered a synthetic material.

In this description of the invention, the term "herbicidal" or "herbicidally effective" refers to the quality of being effective to kill, control or suppress a plant when at least a minimum amount of the herbicide composition contacts the plant. The term "kill" as used herein in relation to a herbicide means to cause the above-ground portion of a plant to irreversibly cease normal function, typically resulting in wilting and browning and/or necrosis of the normally green tissues of the plant. It is, of course, possible that a plant, particularly a perennial plant, that is killed within this meaning, may "re-sprout" and produce new growth. The term control as used herein in relation to a herbicide means that, in a treated area, the plants experience at least about 90% mortality. The term "mortality" as used herein can refer to a percentage of individual plants in the treatment area that are killed, or a percentage of the total mass or total surface area of vegetation in the treatment area that experiences wilting, bleaching, browning or necrosis. The term "suppress" is used herein in relation to a herbicide to mean that, in a treatment area, the plants experience from about 40 to about 90% mortality. Application of an inventive herbicide composition to the plant causes the plant, where contacted, to wilt, bleach, or brown, which results in necrosis of the leaf ("burn down") and oftentimes death of the plant.

Herbicide compositions in accordance with many preferred embodiments of the present invention are nonselective and non-systemic, and are effective against almost any vegetation, specifically against common crop and garden weeds, both annual and perennial. They are "contact herbicides" in that their action results from contact with plant surfaces rather than uptake by the plant. In addition, inventive formulations are "knockdown" (i.e. fast acting, typically within several hours) or "burn down" herbicides, which must be sprayed over a substantial portion of the above-ground part of the plant in order to have an optimal or desired effect. Conveniently, the herbicides are applied as a fine droplet spray. In addition, it is believed that inventive herbicides have optimal burn down effect in relatively warm temperatures and relatively dry conditions (relative to average temperatures and moisture for a given location). The active ingredient of the present herbicidal compositions has the advantage of being an environmentally friendly, natural product, which is unlikely to cause environmental pollution or create toxicity problems for humans or domestic animals. Because limonene-containing oils are natural oils, the non-toxic aqueous herbicide compositions of the invention are environmentally acceptable and have little, if any deleterious effect on humans, wildlife and non-target vegetation.

For purposes of clarity, the term "herbicide composition" is used herein to refer to a liquid that is actually contacted with a plant, such as from a sprayer, to achieve burn down in accordance with the invention. A herbicide composition of the invention can be made and provided to an end user as a pre-made (or "pre-mixed" or "ready to spray") herbicide composition in some forms of the invention. In other forms of the invention, the herbicide composition can be mixed by the end user at or near the place where the herbicide composition will be used by diluting a herbicide concentrate formulation and optionally adding other ingredients. As used herein, the terms "herbicide formulation" and "herbicide concentrate" and "herbicide concentrate formulation" are used interchangeably to refer to a formulation of ingredients in accordance with the invention that can be diluted with water, with the optional addition of other ingredients, to provide a herbicide composition. This manner of providing a herbicide concentrate formulation may be desirable, for example, where vegetation covering a large area is to be sprayed, for example, using commercial spraying equipment, and thus a great volume of the herbicide composition is needed. In such a case, a herbicide formulation can be provided to an end user, optionally together in a kit, with instructions for mixing the formulation with water, and perhaps other ingredients in or near the sprayer to provide a herbicide composition. Such herbicide formulations and herbicide kits are described further herein, but attention is first given to herbicide compositions of the invention.

In accordance with the invention, a non-selective, burn down herbicide composition includes a herbicidally active limonene component, an emulsifying agent and a hydrophilic solvent, preferably water, and that includes a wetting agent, or has a pH greater than 5, or includes a wetting agent and has a pH greater than 5.

The herbicidally active limonene component includes limonene or a limonene derivative in sufficient amount that it is effective, when in a herbicide composition provided in accordance with the present invention, to kill, control or suppress plants that are contacted with a sufficient amount of the herbicide composition. A sufficient amount is considered to be an amount contacting a sufficient surface of the plants to achieve a desired result. The herbicidally active limonene component can be a pure or substantially pure limonene or limonene extract, or a multi-component composition that includes limonene. In this regard, the herbicidally active limonene component can comprise an essential oil that includes limonene, preferably at least about 8% limonene by weight. For example, the limonene can be provided in the form of a citrus oil, a pine oil, eucalyptus oil or a tea tree oil, any of which can be the herbicidally active limonene component in accordance with the invention.

Furthermore, the herbicidally active limonene component can comprise a modified limonene, as long as the modified limonene has herbicidal activity in accordance with the invention. For example, based upon work that has been reported by others, it appears that oxygenation of limonene to provide limonene oxide may improve water solubility characteristics while maintaining similar burn-down functionality compared to unmodified limonene. Such modified limonene compounds are contemplated by the present invention, and are expressly included within the meaning of the term "herbicidally active limonene component."

In one preferred embodiment, the herbicidally active limonene component comprises a citrus oil, e.g. orange oil. In another preferred embodiment, the herbicidally active limonene component comprises d-limonene derived from a citrus oil. The fraction of the citrus oil comprising d-limonene can be separated off by vacuum distillation, or any other conventional separation process. d-Limonene is volatile, and is separated off in the distillate. The distillate is a highly concentrated composition of the d-limonene, comprising about 95-96% by weight of d-limonene and about 4-5% by weight of other components. This distillate may be utilized in a herbicidal composition of the present invention.

Although it is possible to use unrefined citrus oil, instead of the vacuum distillate, as discussed above, vacuum distillation (or other separation process, such as steam distillation (azeotroping), solvent extraction, supercritical extraction etc.) has the advantage of separating the herbicidally active ingredient from flavor components of the citrus oil. The flavor components then form a valuable by-product, which can be utilized in, for example, foodstuffs or pharmaceutical compositions.

Other terpenes, particularly monoterpenes, that have similar herbicidal properties to limonene in formulations as provided herein are considered equivalent to limonene for purposes of the present invention. Similarly, other natural oils having high terpene content and having similar herbicidal properties to the limonene-containing oils discussed above in formulations as provided herein are considered equivalent to the limonene-containing oils for purposes of the present invention. "High terpene content" as used herein means those natural oils having a terpene content of at least 50 per cent. It is preferable that the natural oil contains at least 90 per cent terpene. Such terpenes and terpene containing natural oils are expressly encompassed within the meaning of the term "herbicidally active limonene component" as used herein.

When pure or substantially pure limonene is used in an inventive herbicide concentrate suitable for organic use, the herbicide composition preferably includes from about 8 percent to about 100 percent by weight of the limonene, preferably from about 8 percent to about 90 percent by weight. It is understood by a person of ordinary skill in the art that a herbicide composition having a lower concentration of limonene can be used to achieve a similar response by spraying a higher volume of the herbicide composition on the plant (increasing the volume increases the amount of limonene to which the plant is exposed).

Certain preferred embodiments of the herbicide concentrates suitable for organic use generally contain from about 8% by weight to about 90% by weight limonene and more preferred embodiments generally contain from about 35% by weight to about 85% by weight limonene. Certain preferred embodiments of the ready-to-use formulations and/or the diluted concentrates suitable for organic use generally contain from about 2% by weight to about 25% by weight limonene and more preferred embodiments generally contain from about 10% by weight to about 20% by weight.

When a terpene containing natural oil is used, the amount of the natural oil in the herbicide will depend upon the amount of terpenes in the specific oil used. In one embodiment, the herbicide composition includes from about 8 percent to about 100 percent by weight of such a natural oil, preferably from about 12 percent to about 30 percent by weight and more preferably from about 15 percent to about 25 percent by weight. For a herbicide composition containing limonene to qualify for use in organic production under 37 CFR 205.601, the limonene must be a natural product produced by non-chemical means such as by distillation.

As discussed above, the remainder of the herbicide composition in this embodiment comprises water (or optionally another hydrophilic solvent), one or more emulsifying agents, and one or more of a wetting agent and a pH modifier.

The emulsifying agent is preferably a non-toxic emulsifying agent, and can be a surfactant or other emulsifying agent known in the art, or a mixture of one or more thereof. The emulsifying agents employed should be capable, when mixed with water and the herbicidally active limonene component, of forming an emulsion, preferably a homogeneous emulsion.

Useful emulsifying agents include lauryl dimethyl amine oxide, polyoxypropylene, octylphenol ethoxylates (5EO to 12EO), nonylphenol ethoxylates, polyoxyethylene block copolymers alcohol ethoxylate. Such alkylphenol ethoxylates are available commercially under the tradenames Surfonic® OP-100, Surfonic® OP-120, Surfonic® OP-70, Surfonic® OP-50, Triton X-405 and Triton X-45. Alternatively, the emulsifying agent can be a polyethoxylated castor oil (POE from 16-40). Such emulsifying agents are available commercially under the trade names of Alkamuls® EL620 and Alkamuls® EL-719 originally available from Rhone Poulenc Co, but now owned by Rhodia Inc. located at 259 Prospect Plains Road, Cranbury, N.J. 08512. It is non-toxic to humans and animals and will not cause skin or eye irritation. Surfonic® is a registered trademark of Huntsman Petrochemical Corporation, 500 Huntsman Way, Salt Lake City, Utah 84108. Triton® is a registered trademark of the Dow Chemical Company, Midland, Mich. Alkamuls® is a registered trademark of Rhodia Inc., 259 Prospect Plains Road, Cranbury, N.J. 08512.

Other commercially available emulsifying agents that are non-toxic, such as polyoxyethylenesorbitans supplied by ICI Americas or Sigma Chemical Company, may also be suitably used for the present invention. In a preferred embodiment a polyoxyethylenesorbitan monooleate such as Tween 80 may be used. Tween is a registered trademark of ICI Americas Inc.; 10 Finderne Avenue, Bridgewater, N.J. 088073300 and can be obtained from Sigma-Aldrich, 3050 Spruce St., St. Louis, Mo. 63103.

Surfactants such as anionic and nonionic surfactants are acceptable emulsifying agents for use in a herbicide composition of the present invention. Preferred anionic surfactants include salts of fatty acids, alkyl sulphates, alkyl ether sulphonates and alkyl aryl sulphonates. Preferred nonionic surfactants include nonylphenol ethoxylate surfactants. Examples of preferred surfactants include about 10 per cent sulfonic acid, about 6 per cent to about 7 per cent sodium laurel sulfate, from about 8 per cent to about 12 per cent alcohol ethoxylate and from about 1 per cent to about 2 per cent olefin sulfonate.

In general, the emulsifying agent should be present in an amount sufficient to render the herbicidally active limonene component miscible in the water or other hydrophilic solvent. Generally, the ready-to-use or diluted herbicide composition suitable for organic use will contain from about 0.05 percent to about 15 percent by weight of one or more emulsifying agent, preferably from about 0.5 percent to about 10 percent by weight and more preferably from about 2 percent to about 8 percent by weight. The herbicide concentrate will generally contain from about 1% to about 30% by weight emulsifying agent, more preferably from about 5% to about 20% by weight emulsifying agent.

Herbicides prepared according to embodiments of the present invention for use in organic production include emulsifying agents that are either natural products produced by non-chemical means or a synthetic compound defined by 7 CFR 205.601. As noted above, an inert material can comply with 7 CFR 205.601 by being included on either of the EPA's list 4A or 4B provided in Appendix A. Preferred emulsifiers from testing thus far include the surfactants, (nonylphenol polyoxyethylene 10), (alkylether mono & di-phosphate ester), (2,6,8-trimethyl-4-nonyl ether ethoxylate), ((poly (oxy-1,2-ethanediyl, alpha-(nonylphenyl-omega-hydroxy-), and (octylphenol ethoxylate).

While an inventive herbicide composition will typically comprise an emulsion of a herbicidally active limonene component with water, an inventive composition can include another non-toxic hydrophilic solvent instead of or in addition to water, such as, for example, ethanol, dilute acetic acid solutions, and the like.

As stated above, in one embodiment of the invention, the herbicide composition has a pH greater than 5. In another embodiment, the herbicide composition has a pH of from about 5 to about 10. The pH of the naturally acidic limonene can be raised by including a pH modifier in the herbicide composition. Examples of pH modifiers that can be selected for use in connection with the invention include, without limitation, potassium carbonate, sodium hydroxide and potassium hydroxide. In one preferred embodiment, the pH of the composition can range from about 6 to about 8. In another preferred embodiment, the pH range of the herbicidal composition is from about 8 to about 10.

For embodiments comprising organic formulations, preferred pH modifiers are selected from the group of sodium hydroxide, sodium carbonate, potassium hydroxide, potassium carbonate, calcium hydroxide, and calcium carbonate. Other bases listed in EPA List 4A or 4B can also be used to provide formulations that can be used in organic production according to the present disclosure. Preferred embodiments of the formulations used for organic production typically range from about 6 to about 9.

Thus, in certain preferred embodiments of the invention, herbicide compositions, which are suitable for application as a spray in organic production, include about 8% to about 100% w/w %, preferably about 2% to about 25% w/w %, and more preferably from about 10% to about 20% by weight of a herbicidally active limonene component; from about 0.05% to about 15% w/w %, preferably about 0.5% to about 10% w/w %, and more preferably from about 2% to about 8% by weight of an emulsifying agent; a pH modifier in an amount effective to maintain a desired pH in the composition; and the balance of water or other selected hydrophilic solvent. In one preferred embodiment, there is provided a herbicide composition comprising a herbicidally active limonene component at a concentration of at least about 8% w/w %, an emulsifying agent effective to dissolve or disperse the herbicidally active limonene component in water, in an effective amount, a pH modifier effective to maintain a pH greater than 5, and a hydrophilic solvent, preferably water.

In another embodiment of the invention, the herbicide composition includes a wetting agent effective to improve the wetting properties, and possibly also the penetration properties, of the herbicide composition. When a wetting agent is included in a herbicide composition of the invention, the composition sprayed on the weeds or other vegetation can be applied at a lower rate (i.e., measured in gallons per acre) to achieve an equivalent result because the wetting agent causes each droplet of the composition to spread over a greater surface area of the plant. When a wetting agent is absent, the composition sprayed on a plant must cover a significantly greater surface area of the plant to achieve a similar result.

Many wetting agents suitable for use in herbicides are known to a person of ordinary skill in the art, and are available commercially. Examples of wetting agents that can be selected for use in connection with the invention, including formulations suited for organic production include, without limitation, nonylphenol ethoxylate, octylphenol ethoxylate, and anionic, cationic and nonionic (including silicone based) surfactants and methylated seed oil. In one preferred embodiment suited for organic production, the composition includes from about 0.05% to about 15% w/w % of a wetting agent. In another preferred embodiment suited for organic production, the herbicide composition includes from about 0.5% to about 10% w/w %, more preferably from about 2% to about 8% w/w %, of a wetting agent. For embodiments comprising organic formulations, suitable wetting agents include nonylphenol ethoxylate, octylphenol ethoxylate, dodecyl sulfate, sodium salt, caseins or other wetting agent listed in EPA List 4A or 4B reproduced in Appendix A.

Thus, in certain preferred embodiments of the inventive, herbicide compositions suitable for use in organic production, which are suitable for application as a spray, include about 8% to about 100% w/w %, more preferably about 8% to about 30% w/w %, and more preferably from about 10% to about 20% by weight of a herbicidally active limonene component; from about 0.05% to about 15% w/w %, more preferably about 0.5 to about 10% w/w %, and more preferably from about 2% to about 8% by weight of an emulsifying agent; from about 0.02% to about 1.0% w/w %, more preferably about 0.05% to about 0.5% w/w %, and the balance of water or other selected hydrophilic solvent. In one preferred embodiment, there are provided herbicide compositions comprising a herbicidally active limonene component at a concentration of at least about 8% w/w %, an emulsifying agent effective to dissolve or disperse the herbicidally active limonene component in water, a wetting agent at a concentration of at least about 0.05% w/w % and a hydrophilic solvent, preferably water.

In still another embodiment of the invention, the herbicide composition includes a wetting agent effective to improve the wetting and penetration properties of the composition and has a pH greater than 5. In another embodiment, the herbicide composition, including a wetting agent, has a pH from about 5 to about 10. In yet another embodiment, the pH is from about 6 to about 9. Examples of wetting agents and pH modifiers that can be selected for use in connection with the invention include those described above as non-limiting examples.

Thus, in certain preferred embodiments of the invention suitable for use in organic production, herbicide compositions, which are suitable for application as a spray, include about 8% to about 100% w/w %, more preferably about 8% to about 30% w/w %, and more preferably from about 10% to about 20% by weight of a herbicidally active limonene component; from about 0.05% to about 15% w/w %, more preferably about 0.5% to about 10% w/w %, and more preferably from about 2% to about 8% by weight of an emulsifying agent; a pH modifier in an amount effective to maintain a pH greater than 5; and the balance of water or other selected hydrophilic solvent. In one preferred embodiment, there are provided herbicide compositions comprising a herbicidally active limonene component at a concentration of at least about 8% w/w %, an emulsifying agent effective to dissolve or disperse the a herbicidally active limonene component in water, a wetting agent at a concentration of at least about 0.05% w/w %; a pH modifier effective to maintain a pH greater than 5, and a hydrophilic solvent, preferably water.

The addition of an added oil component to the herbicides discussed above can further increase the herbicide's efficacy, knock down, and long-term killing effect. In testing, so far, the formulations containing as little as 0.05% w/w % of an added oil component have demonstrated a beneficial effect resulting from the presence of the added oil component.

Thus, such further preferred embodiments discussed above, of the novel herbicide compositions suitable for use in organic production, taking into account the added oil component, include about 8% to about 100% w/w %, more preferably about 8% to about 30% w/w %, and more preferably from about 10% to about 20% by weight of a herbicidally active limonene component; from about 0.05% to about 10% w/w %, more preferably about 0.1% to about 8% w/w %, and more preferably from about 0.2% to about 5% by weight of an emulsifying agent; from about 0.02% to about 1.0% w/w %, more preferably about 0.05 to 0.5% and more preferably from about 0.1% to about 0.2% by weight of a wetting agent; a pH modifier in an amount effective to maintain a pH greater than 5; an amount of an added oil component sufficient to increase the herbicide's efficacy and lengthen the herbicide's period of efficacy; and the balance of water or other selected hydrophilic solvent. Based on initial studies, at least about 0.05% w/w % of an added oil component was preferred and from about 0.25% to about 0.5% w/w % of an added oil component was more preferred. However, more recent studies have shown that improved efficacy can be obtained with added oil components utilized in amounts up to about 35% by weight. For example preferred herbicidal concentrates containing from about 2% by weight to about 20% by weight have proven particularly efficacious. More preferred herbicidal concentrates contain from about 4% by weight to about 12% by weight added oil components. Preferred ready-to-use formulations and/or concentrates which have been diluted prior to use contain from about 0.5% to about 6% of the added oil component. The more preferred ready-to-use or diluted concentrates contain from about 1% to about 4% of the added oil component. While not to be bound by theory, it is believed from testing thus far that the added oil component contained in these preferred embodiments results in a better emulsion which retards the volatilization of limonene both before and after application to the plant and facilitates absorption onto leaf surfaces, thus increasing and extending the herbicide's efficacy and both its knockdown and long term ability. The added oil component also thickens the formulation resulting in better adhesion to the plant leaf surfaces.

The herbicide compositions of this invention suitable for use in organic production can be prepared by entirely conventional procedures known to those of ordinary skill in the art. For example, the compositions can be made by preparing an aqueous mixture of the water, the emulsifying agent and the herbicidally active limonene component. The resulting mixture can then be agitated until a dispersion or emulsion is formed. In one manner of making a herbicide composition according to the invention, each non-aqueous component can be added serially into a container, with stirring, preferably for at least about 1 minute after the addition of each component before adding the next component. After all of the non-aqueous components are mixed, the batch is agitated for another 10 minutes and the water can be mixed in to provide the herbicide composition. It can then be tested for quality control, filtered and filled into suitable containers for shipment, storage or immediate use.

The invention has been described thus far in terms of the final herbicide composition, and inventive herbicides can be made, sold and shipped as ready-to-use solutions. It is understood, however, that an excellent manner of providing a herbicide composition to an end user is by first preparing a concentrate formulation that is then diluted with water or other hydrophilic solvent by the end user to provide a herbicide composition for application to target weeds or other vegetation. Thus, herbicide compositions in accordance with the invention can be packaged as ready-to-use herbicides, or can be packaged as herbicide concentrate formulations. Where an inventive herbicide is to be used in a relatively small quantity, such as for home uses, the herbicide can be packaged in a conventional ready-to-use dispensing system. In contrast, when the end user is a farmer or professional applicator who intends to use the herbicide on a large area, it would be more desirable to provide a herbicide concentrate formulation that is ready for dilution. As used herein, the terms "formulation" and "herbicide formulation" are intended to refer to such a concentrate.

In one embodiment, the formulation includes a herbicidally active limonene component mixed with an emulsifying agent. In this embodiment, the formulation, along with a pH modifier, a wetting agent, or both (which can be obtained separately or provided with the formulation in a kit) are mixed with water or other hydrophilic solvent by the end user, for example, in a commercial sprayer. In another embodiment, the pH buffering agent, the wetting agent, or both, are premixed with the herbicidally active limonene component the emulsifying agent to provide a formulation that can be mixed directly with water or other hydrophilic solvent to provide a herbicide composition of course, it is also possible to provide all of the ingredients separately to an end user, with instructions regarding mixing the ingredients together to provide a herbicide composition or a herbicide formulation.

In a particularly preferred embodiment, the herbicide formulation includes a herbicidally active limonene component mixed with an emulsifying agent, and is provided separately from the pH modifier, the wetting agent, or both. A person of ordinary skill in the art will appreciate that the function of the emulsifying agent is to emulsify the herbicidally active limonene component with water, and the amount of emulsifying agent to include in a herbicide formulation or a herbicide composition is related to the amount of limonene in the formulation, irrespective of how diluted the limonene will be in the final herbicide, composition. Thus, whether the herbicide formulation is ultimately mixed with water in a water-to-formulation ratio of, for example, 1:1, 3:1 or higher, the amount of emulsifying agent per unit limonene can remain unchanged. In contrast, the amount of pH modifier that would desirably be included in a herbicide composition can depend upon the volume and the initial pH of water mixed with the formulation; and the amount of wetting agent that would desirably be included in a herbicide composition is dependent upon the total volume of the herbicide composition. Therefore, the emulsifying agent can advantageously be mixed with the herbicidally active limonene component in a herbicide formulation, while the pH modifier and the wetting agent are desirably added at the time the herbicide formulation is mixed with water to provide the final herbicide composition.

In certain preferred embodiments of the invention, there are provided herbicide formulations comprising a herbicidally active limonene component at a concentration of at least about 8% (w/w %), and an emulsifying agent at a concentration of from about 0.5% to about 10% (w/w %). In another embodiment, a herbicide formulation is provided that comprises a herbicidally active limonene component at a concentration of at least about 8% (w/w %), an emulsifying agent at a concentration of from about 0.5 to about 10% (w/w %), and a pH modifier in an amount effective to maintain the pH of the final herbicide composition above 5. In another embodiment, a herbicide formulation is provided that comprises a herbicidally active limonene component at a concentration of at least about 8% (w/w %), an emulsifying agent at a concentration of from about 0.5 to about 10% (w/w %), and a wetting agent at a concentration of from about 0.2% to about 10% (w/w %). In yet another embodiment, a herbicide formulation is provided that comprises a herbicidally active limonene component at a concentration of at least about 8% (w/w %), an emulsifying agent at a concentration of from about 0.5 to about 10% (w/w %), a wetting agent at a concentration of from about 0.2% to about 10 (w/w %); and a pH modifier in an amount effective to maintain the pH of the final herbicide composition above 5.

Said formulations can advantageously be mixed with water, and optionally one or more additional ingredients, at or near the location where the end user intends to apply the herbicide composition to plants. Thus, the invention provides in one aspect a method for making a herbicide composition that includes providing a liquid herbicide formulation, the herbicide formulation including a herbicidally active limonene component and an emulsifying agent; diluting the formulation with water to provide a herbicide composition; and mixing into the herbicide composition a pH modifier effective to provide a pH greater than 5 in the composition. In another aspect, the invention provides a method for making a herbicide composition that includes providing a liquid herbicide formulation, the herbicide formulation including a herbicidally active limonene component and an emulsifying agent; diluting the formulation with water to provide a herbicide composition; and mixing into the herbicide composition a wetting agent. In yet another aspect, there is provided a method for making a herbicide composition that includes providing a liquid herbicide formulation, the herbicide formulation including a herbicidally active limonene component and an emulsifying agent; diluting the formulation with water to provide a herbicide composition; and mixing into the herbicide composition a wetting agent and a pH modifier effective to provide a pH greater than 5. The invention also provides a method for making a herbicide composition that includes providing a liquid herbicide formulation, the herbicide formulation including a herbicidally active limonene component, an emulsifying agent and a pH modifier effective to provide a pH greater than 5 in the formulation; diluting the formulation with water to provide a herbicide composition; and mixing into the herbicide composition a wetting agent.

A herbicidal formulation made or selected in accordance with the present invention can also be packaged or otherwise provided together with additional components in a kit. In one embodiment of the invention, a kit for non-selective burn down of plants is provided that includes a container having therein a liquid herbicide formulation, the herbicide formulation including a herbicidally active limonene component, an emulsifying agent and a pH modifier effective to provide a pH greater than 5; and instructions, recorded in a medium, for diluting the formulation to provide a herbicide composition. In another embodiment, also recorded in the medium are instructions for applying the herbicide composition to a pre-selected area for killing, controlling or suppressing plants growing in the area.

In another embodiment, a kit for non-selective burn down of plants is provided that includes a container having therein a liquid herbicide formulation, the herbicide formulation including a herbicidally active limonene component and an emulsifying agent; and instructions, recorded in a medium, for diluting the formulation with water and adding a pH modifier effective to provide a pH greater than 5. In another embodiment, also recorded in the medium are instructions for applying the herbicide composition to a pre-selected area for indiscriminately killing, controlling or suppressing plants growing in the area.

In another form of the invention, there is provided a kit for non-selective burn down of plants that includes a container having therein a liquid herbicide, the herbicide including water, a herbicidally active limonene component, an emulsifying agent and a wetting agent; and instructions for applying the herbicide to a pre-selected area for killing, controlling or suppressing weeds or other plants in the area.

Also provided by the invention is a kit for nonselective burn down of plants that includes a container having therein a liquid herbicide formulation, the herbicide formulation including a herbicidally active limonene component and an emulsifying agent; and instructions, recorded in a medium, for diluting the formulation and mixing in a wetting agent to provide a herbicide composition. In another embodiment, also recorded in the medium are instructions for applying the herbicide composition to a pre-selected area for killing, controlling or suppressing plants growing in the area.

In another form of the invention, a kit for nonselective burn down of plants is provided that includes a container having therein a liquid herbicide, the herbicide including water, a herbicidally active limonene component, an emulsifying agent, a wetting agent and a pH modifier effective to provide a pH greater than 5; and instructions for applying the herbicide to a pre-selected area for indiscriminately killing plants growing in the area. Another kit for non-selective burn down of plants is provided that includes a container having therein a liquid herbicide formulation, the herbicide formulation including a herbicidally active limonene component, an emulsifying agent and a pH modifier effective to provide a pH greater than 5; and instructions, recorded in a medium, for diluting the formulation and adding a wetting agent to provide a herbicide composition. Still another embodiment of the invention is a kit for non-selective burn down of plants that includes a container having therein a liquid herbicide formulation, the herbicide formulation including a herbicidally active limonene component and an emulsifying agent; and instructions, recorded in a medium, for diluting the formulation with water and adding a wetting agent and a pH modifier effective to provide a pH greater than 5.

In addition to inclusion of herbicide formulations in a kit, as described above, the invention also contemplates providing a pre-made, complete herbicide composition with other components in a kit. Thus, in another, form of the invention, a kit for non-selective burn down of plants is provided that includes a container having therein a liquid herbicide, the herbicide including water, a herbicidally active limonene component, an emulsifying agent and one or more member selected from a wetting agent and a pH modifier effective to provide a pH greater than 5; and instructions, recorded in a medium, for applying the herbicide to a pre-selected area for indiscriminately killing plants growing in the area.

An inventive herbicide composition or herbicide concentrate formulation in accordance with the invention can be prepared to include a variety of other beneficial ingredients in addition to the ingredients discussed above. By "beneficial", it is meant that the additional ingredient provides some additional functionality, efficacy, quality or other desirable attribute the herbicide or herbicide concentrate. For example, the herbicidally active limonene component may be blended with other, cheaper, and somewhat less volatile oils to form effective herbicides. Various natural oils (such as cottonseed oil, soybean oil, rapeseed oil, sunflower oil, safflower oil, olive oil, coconut oil, coconut milk, corn oil, grape seed oil and peanut oil) have been reported by others to lack significant herbicidal activity; however, they can be blended with the herbicidally active limonene component of the present invention to form effective herbicidal compositions.

As discussed previously, it has also been discovered that the further addition of an added oil component, whether natural or processed, has proven beneficial to the preferred methods, kits and compositions described herein, increasing the herbicidal effectiveness of the embodiments as to immediate knockdown effect and to long term killing ability as well. For example, testing performed thus far has shown that the presence of such ethoxylated derivatives of castor oil have proven particularly useful as an added oil component as illustrated in Examples 4-7 below. As described above, based on testing performed thus far, this added oil component is preferred to be present in an amount of at least about 0.05% w/w % and in more preferred amounts of from about 0.25% to about 0.5% w/w %. For embodiments comprising organic formulations, preferred oils include oils that are either natural products obtained by non-chemical processes or oils listed in EPA List 4A or 4B, such as for example castor oil, cottonseed oil, soybean oil, sunflower oil, pine oil, coconut oil and their ethoxylated derivatives.

One or more other ingredients may optionally be included in the compositions of the invention in order to provide aesthetic or other beneficial properties thereto. Such optional ingredients are, for example, antimicrobial agents, preservatives, deodorizers, coloring agents, fragrances, additional emulsifiers, additional solubilizers, corrosion inhibitors and additional solvents. The only requirement is that for any particular composition such optional ingredients be compatible with the other ingredients present in the composition or formulation.

By way of example, optional ingredients that can be incorporated include the following: an antimicrobial, such as, for example, phenolic compounds such as ophenylphenol and o-benzyl[p-chlorophenol]; quaternary ammonium compounds such as alkyldimethylbenzylammonium chloride, octyldecyldimethylammonium chloride, dioctyldimethylammonium chloride, didecyldimethylammonium chloride and alkyldimethylbenzylammonium saccharinate; a deodorizer, such as, for example, N-alkyl-N-ethylmorpholinium ethyl sulfate; and a corrosion inhibitor, such as, for example, mono- and triethanolamine, ammonium hydroxide, sodium molybdate, sodium benzoate and tetra sodium ethylenediamine tetraacetate.

Other optional ingredients, as well as the amounts of the optional ingredients that can be employed, can readily be determined by one skilled in the art. For example, the phenolic and quaternary ammonium antimicrobial agents generally will not exceed a concentration of about 0.2 percent by weight in the final herbicide composition.

In order to provide a reasonable shelf-life to the herbicide compositions, it is preferable that a preservative be added to the composition. One such suitable preservative is sodium benzoate commercially supplied by Pfizer, Inc. Other commercially available preservatives used for preserving food, as would be known to those of ordinary skill in the art, may also be suitably used.

The beneficial agents described above, and many others, as would be contemplated by a person of ordinary skill in the art, are well known to those skilled in the art and are available commercially.

In a further aspect, the invention provides a method for killing, controlling or suppressing unwanted plant growth, wherein a herbicide composition provided in accordance with the present invention is applied to the unwanted plant or plants. The composition is then permitted to remain in contact with the plant, preferably the leaves of the plant, for a period of time sufficient to kill, control or suppress the plant. The time required for effective treatment of a given plant is dependent upon a variety of factors including, but not limited to concentration, spray coverage, pH of the herbicide solution, the species of the plant, the size/age/maturity of the plant, the availability of leaf surfaces or other green surfaces, and ambient conditions.

In an agricultural setting, spray applications with standard equipment typically use 20 to 35 gallons per acre for good coverage. Commercial electrostatic sprayers can bring the rates down significantly to less than 10 gal/acre and still achieve good coverage. In one manner of practicing the invention, the method includes spraying the herbicide on the area at a rate of from about 5 gal/acre to about 40 gal/acre. In another preferred manner of practicing the invention, the method includes spraying the herbicide on the area at a rate of from about 5 gal/acre to about 35 gal/acre.

In a homeowner or professional landscaping setting, spray applications on weeds are typically susceptible to runoff. Depending concentration of the herbicidally active limonene component in the herbicide composition as well as the density and maturity/size of the weeds, the equivalent spray volume per acre could be from a couple of quarts to 100 gallons per acre or more.

The invention will be further described with reference to the following specific Examples. It will be understood that these Examples are intended to be illustrative and not restrictive in nature.

EXAMPLE 1

Preparation of Herbicide Formulation

A herbicide formulation (MM-01) was prepared in accordance with the invention to include 94.0 w/w % limonene with the following emulsifiers: 1.3 w/w % Tergitol™ NP-8 (nonylphenol ethoxylate surfactant), 2.0 w/w % Tergitol™ NP-9 (nonoxynol 9.5 surfactant) and 2.7 w/w % Pluracol® P-425 (polypropylene glycol surfactant). The resulting formulation contains 88% limonene w/w %. For making a 100 gallon batch of this herbicide formulation, each component is added one by one and the mixture is stirred for 10 minutes after each addition and before adding the next component, to ensure complete and homogeneous blending of the components. After all the components are mixed, the batch is agitated for another 10 minutes, tested for quality control, filtered and filled into suitable containers.

Preparation of Herbicide Composition

The formulation was diluted with water to a 3:1 ratio by volume, represented as water:herbicide formulation ratio, to provide a herbicide composition (22% limonene w/w %). It is estimated that the pH of the 3:1 ratio composition was 4.5. The pH was lowered to 4 with lemon juice in a first test batch and raised to pH 9 with potassium carbonate in a second test batch. In addition, a herbicide composition with the 3:1 ratio was modified by adding 0.05% silicone based surfactant (Silwet) in a third test batch.

Protocol for Testing Herbicide Compositions

This field trial was conducted in Northern California during November, 2004. Each of the herbicide compositions described above was sprayed onto postemergent plants with backpack spray equipment to ensure good coverage without runoff. Primary weeds evaluated were Bermuda grass, fescue, and strawberry clover.

Color and wilting ratings were taken at 2 hours, 1 day, 2 days, and 7 days after treatment. Data collected for the test compositions were compared to an untreated control (UTC) and an area of vegetation treated with Paraquat (Gramoxone®). This trial contained 3 reps per treatment (except the Paraquat treatment which was a single strip). Treatments were randomly distributed within a rep. Color and wilting ratings were taken at 2 hours, 1 day, 2 days and 7 days after treatment. Results are set forth in FIGS. 1-6.

Discussion

In this trial, in which all treatment received 3:1 ratios (water:limonene formulation), the plants responded very rapidly. In broadleaf plants, discoloration followed by necrosis, and blackening of the leaf tissue occurred within 2 to 4 hours. In grasses, the response was more gradual, and leaves tended to gradually change from green to yellow to brown.

All MM-01 treatments resulted in a visual, burn down response within 2 hours. After Day 1, all MM-01 treatments were significantly different (P<0.05) from the untreated control (UTC).

The best MM-01 treatments were with 0.05% silicone surfactant and at pH 9. At days 2 and 7, both were significantly better than the other treatments. At days 2 and 7, the surfactant and pH 9 treatments were numerically equivalent to the Paraquat standard.

Wilting responses increased over time for all MM01 treatments. Color ratings for MM-01 did not change significantly over time.

The differences attributed to pH and surfactant are very apparent. In the 7 days after treatment, the impact of surfactant on wilting and color was tallied and the results are set forth in Table I below:

TABLE I

| Effect Measured | MMO1 3:1 ratio (pH 4.5) | MMO1 (3:1 ratio) +0.05% | Difference | Difference |
|---|---|---|---|---|
| Wilting | 2.67 | 3.33 | 0.6 | 24.7% |
| Color | 3.67 | 5.00 | 1.33 | 36.2% |
| Average differences | | | 1.00 | 30.5% |

At 7 days after treatment, the impact of pH on wilting and color was also tallied, and the results are set forth in Table II below:

TABLE II

| Effect | pH 4 | pH 9 | Difference | Difference |
|---|---|---|---|---|
| Wilting | 3.00 | 3.67 | 0.67 | 22.3% |
| Color | 3.33 | 4.67 | 1.34 | 40.2% |
| Average differences | | | 1.01 | 31.3% |

The use of a nonionic, silicon surfactant increased the wilting ratings by 24.7% and color by 36.2%.

The use of pH 9 increased the wilting ratings by 22.3% and color by 40.2%.

EXAMPLE 2

Figure 7:
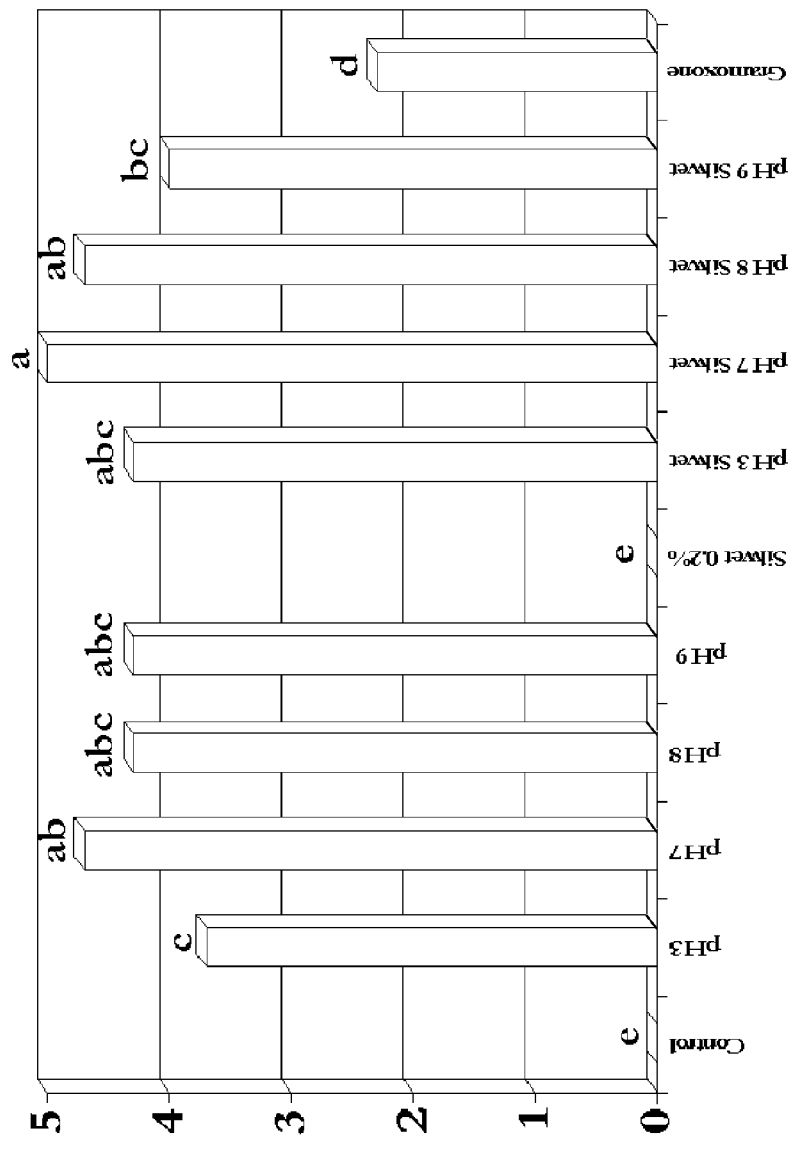
FIG. 7 is a bar graph setting forth results from a field study on lambsquarters conducted in Florida in January of 2005. Ratings are based on 0 to 10 (no damage to dead). Statistical analysis is by Duncan's MRT (P<0.05). Treatments with the same letter or letter combination are not significantly different.

A field trial was conducted in Zellwood, Fla. The same formulation described in Example 1 was used in the Florida trial. All limonene treatments were made at a 3:1 ratio by volume, represented as water:herbicide formulation ratio, to provide a herbicide composition of 22% limonene (w/w %). Four reps per treatment were used; all treatments were randomly distributed within a rep. The weed species was common lambsquarters (1 to 2 feet in height). Treatments applied were pH 3, 7, 8 and 9 with and without a silicone surfactant, Silwet; each treatment was sprayed until runoff. The commercial burn down standard, Gramoxone (Paraquat) was included. Readings were taken at 1 and 2 hours, and 1, 3 and 7 days. An immediate wilting of the lambsquarters was observed with all limonene treatments starting at 1 hour. Effects with Gramoxone (Paraquat) were first observed on day 1 and improved by Day 3. After the first 2 hours limonene effects were stabilized. Results after 3 days are set forth in FIG. 7.

Large common lambsquarters are a difficult to control weed for limonene, making it a good candidate to evaluate difference caused by pH and surfactants. Evaluating the effect of pH, pH 7 gave the best response with and without surfactant. Without surfactant, it was significantly better than pH 3.

Side by side comparisons with the surfactant can also be made. Although not statistically significant, surfactant increased limonene activity with almost every pH with an average increase of 6.1% (see Table)

TABLE III

| Treatment | pH | pH + Silwet | Difference | % Difference |
|---|---|---|---|---|
| pH 3 | 3.7 | 4.3 | 0.6 | 16.2% |
| pH 7 | 4.7 | 5.0 | 0.3 | 6.4% |
| pH 8 | 4.3 | 4.7 | 0.4 | 9.3% |
| pH 9 | 4.3 | 4.0 | −0.3 | −7.5% |
| Average differences | | | 0.25 | 6.1 |

EXAMPLE 3

A series of trials were conducted at Michigan State University (MSU) in East Lansing, Mich. to optimize the response with limonene on key weeds. Grasses responded strongly to limonene, which diminishes their suitability for pH and surfactant evaluations since all treatments gave an excellent herbicidal response. Mature common lambsquarters does not respond well to limonene making it a good candidate for these trials.

Figure 8:
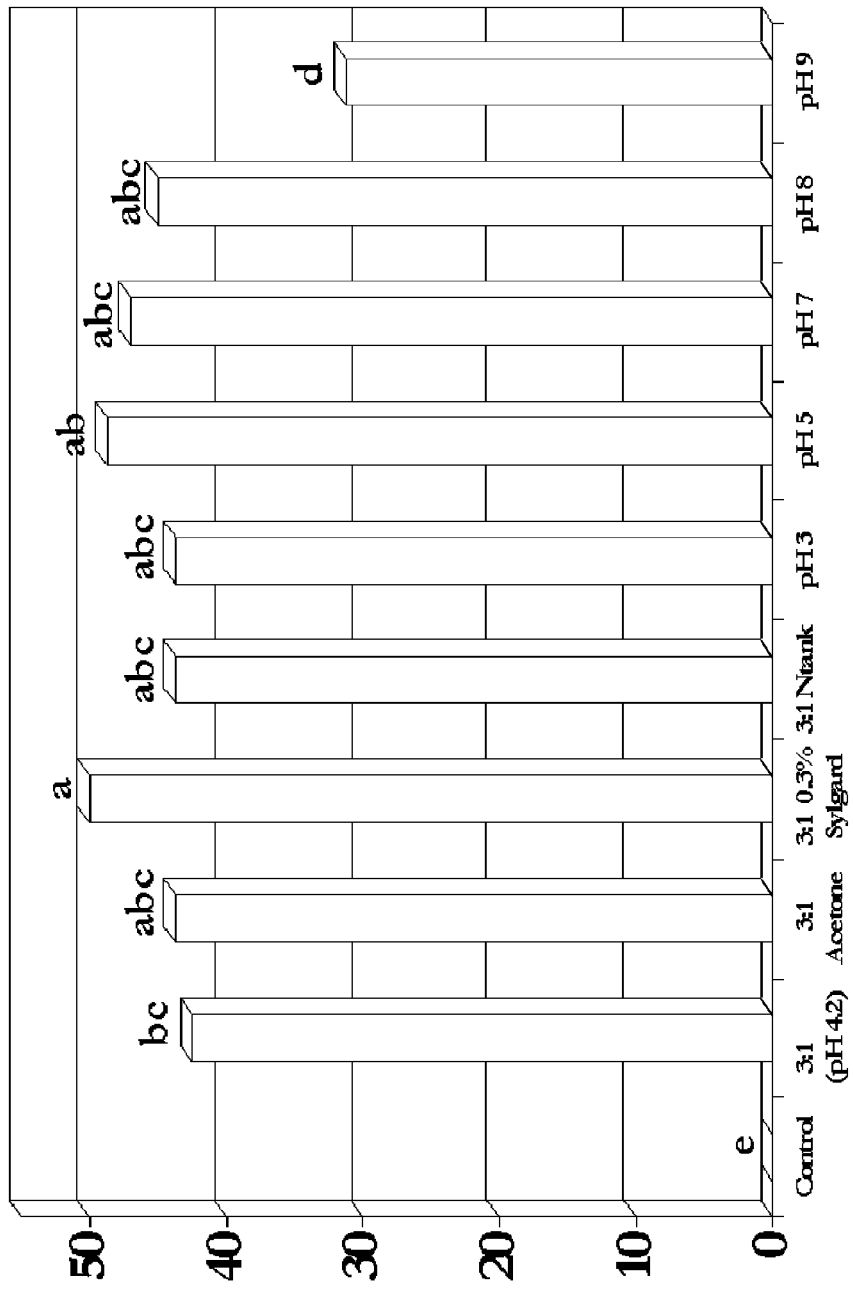
FIG. 8 is a bar graph setting forth results from a greenhouse study on lambsquarters conducted in Michigan in January of 2005. Ratings are based on 0 to 100% (no damage to dead). Statistical analysis is by Duncan's MRT (P_<0.05). Treatments with the same letter or letter combination are not significantly different.

The same formulation described in Example 1 was used in the MSU greenhouse trials. Four reps per treatment were used. All limonene treatments were made at a 3:1 ratio by volume, represented as water:herbicide formulation ratio, to provide a herbicide composition of 22% limonene (w/w %). The herbicide composition was applied in spray chamber designed to mimic an agricultural application. Spray volume was 60 gallons per acre and the spray nozzle pressure was 40 psi. The weed species was common lambsquarters (1 to 2 feet in height). Treatments applied were pH 3, 5, 7, 8 and 9 without any surfactant. A single reading was taken at day 4. Results are set forth in FIG. 8.

There was a strong trend towards a pH response with pH 5 being the optimal pH. pH 7 and 8 had numerically better responses than pH 3 (11.4% and 7.5% respectively) or unadjusted limonene at pH 4.2 (14.7% and 10.6% respectively). pH 9 was significantly lower than the other treatments.

All surfactants improved the performance of the limonene formulation in water. The silicon based product, Sylgard, was significantly better by comparison.

A further series of greenhouse test treatments, as described below in Examples 4-7, were also conducted at Michigan State University (MSU). Weeds, typically in the 4-8 leaf stage, were contacted with control and test formulations. The spray volume used was 60 gallons per acre with a spray pressure of 40 psi. Plant conditions were determined and the percent control evaluated one day after treatment (Examples 4-5) and additionally five days after treatment (Examples 6-7). For all of these Examples, percentages (%) of components are always being given as weight percents (w/w %) of the total composition unless specifically indicated otherwise.

EXAMPLE 4

Common lambsquarter (*Chenopodium album*) was contacted with each of 6 different compositions, formulated as follows: 1) deionized water alone (control); 2) 21.6% d-limonene, 5% alcohol ethoxylate (BIO-SOFT® N25-7), 1.3% castor oil ethoxylate (TOXIMUL® 8242), and the balance water; 3) 21.6% d limonene alone in water; 4) 10% of an BIO-SOFT® N25-7 in water; 5) 5% TOXIMUL® 8242 and 3% hydrogen peroxide (to increase water solubility of the TOXIMUL® 8242) in water; and 6) 5% TOXIMUL® 8242 alone in water. BIO-SOFT® and TOXIMUL® 8242 are registered trademarks of The Stepan Company, 22 W Frontage Rd Northfield, Ill. 60093. The results of these tests and observations are provided in Table IV below.

TABLE IV

| Treatment # | Limonene % | TOXIMUL® 8242% | BIO-SOFT® N25-7 Surfactant % | Water % | % $H_2O_2$ | % control (1) day after treatment |
|---|---|---|---|---|---|---|
| 1 | 0 | 0 | 0 | 100.00 | 0 | 0 c* |
| 2 | 21.6 | 1.3 | 5 | 77.10 | 0 | 35 a* |
| 3 | 21.6 | 0 | 0 | 78.40 | 0 | 0 c* |
| 4 | 0 | 0 | 10 | 90.00 | 0 | 8 b* |
| 5 | 0 | 5 | 0 | 92.00 | 3 | 0 c* |
| 6 | 0 | 5 | 0 | 95.00 | 0 | 0 c* |

*Treatments with the same letter are not statistically significant ($P < 0.05$).

As can be seen in Table IV, the formulations in Treatments 1, 3, 5 and 6 resulted in no practical effect on the treated plants. While the surfactant, BIO-SOFT® N25-7 (Treatment 4) had some effect, the preferred embodiment of the invention in Treatment 2 had substantially better herbicide performance controlling on the lambsquarter in only one day's time.

EXAMPLE 5

The study conducted in Example 4 was repeated with giant foxtail (*Setaria faberi*). The results are provided in Table V below.

TABLE V

| Treatment # | Limonene % | TOXIMUL® 8242% | BIO-SOFT® N25-7 Surfactant % | Water % | % $H_2O_2$ | % control (1) day after treatment |
|---|---|---|---|---|---|---|
| 7 | 0 | 0 | 0 | 100.00 | 0 | 0 c* |
| 8 | 21.6 | 1.3 | 5 | 77.10 | 0 | 46 a* |
| 9 | 21.6 | 0 | 0 | 78.40 | 0 | 14 b* |
| 10 | 0 | 0 | 10 | 90.00 | 0 | 13 b* |
| 11 | 0 | 5 | 0 | 92.00 | 3 | 0 c* |
| 12 | 0 | 5 | 0 | 95.00 | 0 | 0 a* |

*Treatments with the same letter are not statistically significant (P < 0.05).

Once again, as can be seen in Table V, the formulations in Treatments 7, 11, and 12 resulted in no practical effect on the treated plants. While the surfactant, BIO-SOFT® N25-7 (Treatment 10) and limonene alone (Treatment 9) had some effect, the preferred embodiment of the invention in Treatment 8 had substantially better herbicide performance on the giant foxtail in only one day's time.

EXAMPLE 6

Common lambsquarter (*Chenopodium album*) was contacted here with nine different formulations illustrated in Table VI below. Both one day and five days after treatment, plant conditions were examined and the percent control evaluated through visual observation. The results are provided in Table VI below.

TABLE VI

| Treatments # | Limonene % | TOXIMUL® 8242% | BIO-SOFT® N25-7 Surfactant % | Water % | % Control (Days after Treatment) | |
|---|---|---|---|---|---|---|
| | | | | | (1) | (5) |
| 13 | 0 | 0 | 0 | 100.00 | 0 e* | 0 f* |
| 14 | 21.6 | 0 | 0 | 78.40 | 30 d* | 20 e* |
| 15 | 21.6 | 0 | 2.5 | 75.90 | 40 c* | 18 e* |
| 16 | 21.6 | 0.25 | 2.5 | 75.65 | 50 b* | 35 d* |
| 17 | 21.6 | 0.38 | 2.5 | 75.52 | 46 bc* | 34 d* |
| 18 | 21.6 | 0.25 | 2.5 | 75.65 | 53 b* | 39 cd* |
| 19 | 21.6 | 0.25 | 3.75 | 74.40 | 69 a* | 49 ab* |
| 20 | 21.6 | 0.25 | 4.38 | 73.77 | 70 a* | 45 bc* |
| 21 | 21.6 | 0.25 | 5.0 | 73.15 | 73 a* | 55 a* |

*Treatments with the same letter are not statistically significant (P < 0.05).

As can be seen in Table VI, the formulations in Treatments 15-21 show an increased herbicidal effect with increasing quantities of TOXIMUL® 8242 and/or BIO-SOFT® N25-7 compared to Treatment 13 (the control) and Treatment 14 (aqueous Limonene alone). After one day, treatments 19-21 demonstrated substantially better herbicide performance on lambsquarter in only one day's time.

EXAMPLE 7

Velvetleaf (*Abutilon theoprasti*) was contacted here with nine more formulations composed as illustrated in Table VII below. Both one day and five days after treatment, plant conditions were examined and the percent control evaluated through visual observation. The results are provided in Table VII below.

EXAMPLE 9

The following ingredients were combined in sequence with stirring to provide a homogeneous blend:
70 parts by weight D-limonene,
10 parts by weight pine oil,
7 parts by weight castor oil, ethoxylated (POE40)
5.5 parts by weight nonylphenol ethoxylated (10 mole)
7.5 parts by weight octylphenol ethoxylate (5EO)

Three parts by weight water were slowly added to one part by weight of the blend with continued stirring and stirring continued for about 15 minutes following the addition of water. A ready-to-use (RTU) microemulsion of the herbicide suitable for organic production resulted.

Three parts by weight water were slowly added to one part by weight of the blend with continued stirring and stirring continued for about 15 minutes following the addition of water. The resulting emulsion was suitable for use as a herbicide in an agricultural setting for organic production.

EXAMPLE 10

Lambsquarter (*Chenopodium album*) and Giant Foxtail (*Setaria faberi*) were contacted here with a control solution and the two emulsions described in Examples 8 and 9 above to provide the results illustrated in Table VIII below. Both one day and two days after treatment, plant conditions were examined and the percent control evaluated through visual observation.

TABLE VII

| Treatments # | Limonene % | TOXIMUL® 8242% | BIO-SOFT® N25-7 Surfactant % | Water % | % Control (Days after Treatment) (1) | (5) |
|---|---|---|---|---|---|---|
| 22 | 0 | 0 | 0 | 100.00 | 0 f* | 0 f* |
| 23 | 21.6 | 0 | 0 | 78.40 | 19 e* | 48 e* |
| 24 | 21.6 | 0 | 2.5 | 75.90 | 58 d* | 65 cd* |
| 25 | 21.6 | 0.25 | 2.5 | 75.65 | 71 abc* | 68 bcd* |
| 26 | 21.6 | 0.38 | 2.5 | 75.52 | 70 bc* | 69 abc* |
| 27 | 21.6 | 0.25 | 2.5 | 75.65 | 69 bc* | 69 abc* |
| 28 | 21.6 | 0.25 | 3.75 | 74.40 | 75 ab* | 70 ab* |
| 29 | 21.6 | 0.25 | 4.38 | 73.77 | 75 ab* | 70 ab* |
| 30 | 21.6 | 0.25 | 5.0 | 73.15 | 78 a* | 73 a* |

*Treatments with the same letter are not statistically significant (P < 0.05) . . .

As can be seen in Table VII, the formulations in Treatments 25-30 show an increased herbicidal effect with increasing quantities of TOXIMUL® 8242 and/or BIO-SOFT® N25-7 compared to Treatment 22 (the control), Treatment 23 (aqueous limonene alone) and Treatment 24 (aqueous BIO-SOFT® N25-7 alone). Treatments 25-30 had substantially better herbicide performance on velvetleaf in only one day's time.

EXAMPLE 8

The following ingredients were combined in sequence with stirring to provide a homogeneous blend:
76 parts by weight D-limonene
6 parts by weight pine oil
6 parts by weight castor oil, ethoxylated (POE40)
5 parts by weight nonylphenol ethoxylated (10 mole)
7 parts by weight octylphenol ethoxylate (5EO)

TABLE VIII

| Trial | Plant | Treatment | % Control 1DAT | % Control 2DAT |
|---|---|---|---|---|
| 1 | Common Lambsquarters | CONTROL | 0b | 0b |
| 2 | Common Lambsquarters | Example 8 Microemulsion | 92a | 92a |
| | LSD (0.05) | | 7 | 7 |
| 3 | Giant Foxtail | CONTROL | 0c | 0d |
| 4 | Giant Foxtail | Example 8 Microemulsion | 98a | 99a |
| 5 | Giant Foxtail | Example 9 Emulsion | 90a | 89a |
| | LSD (0.05) | | 20 | 15 |

% Control refers to herbicidal activity, with 0% representing no effect and 100% representing plant death.
DAT is for Days After Treatment.
Treatments with the same letters are not statistically significant (P ≦ 0.05)

EXAMPLE 11

Barnyardgrass (*Echinochloa crus-galli*) and Velvetleaf (*Abutilon theoprasti*) were contacted here with a control solution and the two emulsions described in Examples 8 and 9 above to provide the results illustrated in Table IX below. At one hour, 18 hour and two days after treatment, plant conditions were examined and the percent control evaluated through visual observation.

TABLE IX

| Trial | Plant | Treatment | % Control 1 hr. after treatment | % Control 18 hr. after treatment | % Control 2 DAT |
|---|---|---|---|---|---|
| 6 | Barnyardgrass | CONTROL | 0d | 0c | 0c |
| 7 | Barnyardgrass | Example 9 Emulsion | 80b | 95a | 100a |
| 8 | Barnyardgrass | Example 8 Microemulsion | 90a | 95a | 100a |
|  |  | LSD (0.05) | 2 | 5 | 6 |
| 9 | Velvetleaf | CONTROL | 0c | 0c | 0c |
| 10 | Velvetleaf | Example 8 Microemulsion | 88a | 95a | 98a |
| 11 | Velvetleaf | Example 9 Emulsion | 50b | 73b | 76b |
|  |  | LSD (0.05) | 9 | 3 | 4 |

% Control refers to herbicidal activity, with 0% representing no effect and 100% representing plant death.
DAT is for Days After Treatment.
Treatments with the same letters are not statistically significant ($P \leq 0.05$)

A comparison of the level of control achieved with the herbicide formulations suitable for use in organic production above (Examples 10 and 11) to the earlier control of Lambsquarters, Velvetleaf and Giant Foxtail demonstrates a higher level of control for the formulations tested. Additionally the formulations prepared in Examples 8 and 9 and tested above are suitable for use in organic production under the USDA's National Organic Program.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected.

APPENDIX A

U.S. Environmental Protection Agency
List of Inert Pesticide Ingredients

| CAS # | Name |
|---|---|
| | List A |
| 50-70-4 | Sorbitol |
| 50-81-7 | L-Ascorbic acid |
| 50-99-7 | Dextrose |
| 56-81-5 | Glycerin |
| 57-10-3 | Hexadecanoic acid |
| 57-11-4 | Stearic acid |
| 57-13-6 | Urea |
| 57-50-1 | Sugar |
| 62-54-4 | Calcium acetate |
| 63-42-3 | D(+)-Lactose |
| 68-04-2 | Sodium citrate |
| 77-92-9 | Citric acid |
| 97-64-3 | Ethyl lactate |
| 110-17-8 | Fumaric acid |
| 110-27-0 | Isopropyl myristate |
| 111-03-5 | 9-Octadeceneoic acid (Z)-,2,3-dihydroxypropyl ester (9Cl) |
| 112-80-1 | Oleic acid |
| 121-33-5 | Vanillin |
| 123-95-5 | Butyl stearate |
| 124-38-9 | Carbon dioxide |
| 127-08-2 | Potassium acetate |
| 127-09-3 | Sodium acetate |
| 137-66-6 | Ascorbyl palmitate |
| 138-22-7 | Butyl lactate |
| 142-18-7 | Dodecanoic acid, 2,3-dihydroxypropyl ester |
| 143-07-7 | Dodecanoic acid |
| 143-18-0 | 9-Octandecenoic acid (Z)-, potassium salt |
| 143-19-1 | 9-Octandecenoic acid (Z)-, sodium salt |
| 144-33-2 | Citric acid, disodium salt |
| 144-55-8 | Sodium bicarbonate |
| 298-14-6 | Potassium bicarbonate |
| 471-34-1 | Calcium carbonate |
| 532-32-1 | Benzoic acid, sodium salt |
| 544-63-8 | Myristic acid |
| 546-93-0 | Magnesium carbonate |
| 553-70-8 | Benzoic acid, magnesium salt |
| 557-04-0 | Octadecanoic acid, magnesium salt |
| 557-05-1 | Octadecanoic acid, zinc salt |
| 582-25-2 | Benzoic acid, potassium salt |
| 589-68-4 | Tetradecanoic acid, 2,3-dihydroxypropyl ester |
| 593-29-3 | Octadecanoic acid, potassium salt |
| 764-71-6 | Potassium octoate |
| 813-94-5 | Citric acid, calcium salt (2:3) |
| 822-16-2 | Octadecanoic acid, sodium salt |
| 557-05-1 | Zinc stearate |
| 813-94-5 | Calcium citrate |
| 866-83-1 | Citric acid, monopotassium salt |
| 866-84-2 | Citric acid, tripotassium salt |
| 994-36-5 | Citric acid, sodium salt |
| 1002-89-7 | Ammonium stearate |
| 1302-78-9 | Bentonite |
| 1309-37-1 | Iron oxide ($Fe_2O_3$) |
| 1309-48-4 | Magnesium oxide |
| 1314-13-2 | Zinc oxide |
| 1317-60-8 | Hematite |
| 1317-61-9 | Iron oxide |
| 1317-65-3 | Limestone (no asbestos and less than 1% crystalline silica) |
| 1318-00-9 | Vermiculite (no asbestos and less than 1% crystalline silica) |
| 1318-02-1 | Zeolites (excluding erionite (CAS Reg. No. 66733-21-9)) |
| 1318-93-0 | Montmorillonite |
| 1323-83-7 | Octadecanoic acid, diester with 1,2,3-propanetriol (9Cl) |
| 1327-36-2 | Mullite |
| 1327-43-1 | Aluminum magnesium silicate |
| 1327-44-2 | Aluminum potassium silicate |
| 1332-09-8 | Pumice |
| 1332-58-7 | Kaolin (no asbestos and less than 1% crystalline silica) |
| 1335-30-4 | Aluminum silicate, hydrated |
| 1343-88-0 | Magnesium silicate |
| 1343-90-4 | Magnesium silicate, hydrate |
| 1344-00-9 | Silicic acid, aluminum sodium salt |
| 1344-95-2 | Calcium silicate |
| 1345-25-1 | Iron oxide (FeO)($Fe_2O_3$), ($Fe_3O_4$) |

APPENDIX A-continued

U.S. Environmental Protection Agency
List of Inert Pesticide Ingredients

| CAS # | Name |
|---|---|
| 1393-03-9 | Soapbark (Quillaja saponin) |
| 1406-18-4 | Vitamin E |
| 1592-23-0 | Octadecanoic acid, calcium salt |
| 1863-63-4 | Benzoic acid, ammonium salt |
| 1984-06-1 | Octadecanoic acid, sodium salt |
| 2090-05-3 | Benzoic acid, calcium salt |
| 3609-96-9 | Citric acid, dipotassium salt |
| 5323-95-5 | 9-Octadecenoic acid, 12-hydroxy-, monosodium salt, (9Z,12R) |
| 5743-26-0 | Calcium acetate, monohydrate |
| 5949-29-1 | Citric acid, monohydrate |
| 6100-05-6 | Citric acid, tripotassium salt, monohydrate |
| 6107-56-8 | Calcium octanoate |
| 6132-04-3 | Sodium citrate dihydrate |
| 6858-44-2 | Sodium citrate pentahydrate |
| 6915-15-7 | Malic acid |
| 7440-44-0 | Carbon |
| 7447-40-7 | Potassium chloride |
| 7487-88-9 | Sulfuric acid, magnesium salt (1:1) |
| 7492-30-0 | 9-Octadecenoic acid, 12-hydroxy-, monopotassium salt, (9Z,) |
| 7631-86-9 | Silicon dioxide (crystalline - free forms only) |
| 7646-93-7 | Potassium bisulfate |
| 7647-14-5 | Sodium chloride |
| 7693-13-2 | Citric acid, calcium salt (2:3) |
| 7699-41-4 | Silica, amorphous, precipitated and gel |
| 7704-34-9 | Sulfur |
| 7727-37-9 | Nitrogen |
| 7727-73-3 | Sulfuric acid, disodium salt, decahydrate |
| 7732-18-5 | Water |
| 7757-82-6 | Sodium sulfate |
| 7778-18-9 | Calcium sulfate |
| 7778-49-6 | Citric acid, potassium salt |
| 7778-80-5 | Potassium sulfate |
| 7782-42-5 | Graphite (no asbestos and less than 1% crystalline silica) |
| 8001-22-7 | Soybean oil |
| 8001-23-8 | Safflower oil |
| 8001-25-0 | Olive oil |
| 8001-26-1 | Linseed oil (unboiled) |
| 8001-29-4 | Cottonseed oil |
| 8001-30-7 | Corn oil |
| 8001-31-8 | Coconut oil |
| 8001-78-3 | Castor oil, hydrogenated |
| 8001-79-4 | Castor oil |
| 8002-03-7 | Peanut oil |
| 8002-24-2 | Sperm oil |
| 8002-31-1 | Cocoa |
| 8002-43-5 | Lecithins |
| 8002-48-0 | Malt extract |
| 8002-74-2 | Paraffin wax |
| 8002-75-3 | Palm oil |
| 8006-54-0 | Lanolin |
| 8006-95-9 | Wheat germ oil |
| 8007-69-0 | Almond oil |
| 8008-74-0 | Sesame seed oil |
| 8012-89-3 | Beeswax |
| 8013-17-0 | Invert sugar |
| 8015-86-9 | Carnuba wax |
| 8016-13-5 | Fish oil |
| 8016-70-4 | Hydrogenated soybean oil |
| 8028-66-8 | Honey |
| 8029-43-4 | Corn syrup |
| 8030-76-0 | Lecithins, soya |
| 8031-18-3 | Fuller's earth |
| 8042-47-5 | White mineral oil (petroleum) |
| 8052-35-5 | Molasses |
| 9000-07-1 | Carrageenan |
| 9000-11-7 | Cellulose, carboxymethyl ether |
| 9000-30-0 | Guar gum |
| 9000-40-2 | Carob gum (locust bean gum) |

APPENDIX A-continued

U.S. Environmental Protection Agency
List of Inert Pesticide Ingredients

| CAS # | Name |
|---|---|
| 9002-88-4 | Polyethylene |
| 9004-32-4 | Cellulose carboxymethyl ether, sodium salt |
| 9004-34-6 | Cellulose |
| 9004-35-7 | Cellulose acetate |
| 9004-53-9 | Dextrins |
| 9004-62-0 | Cellulose, 2-hydroxyethyl ether |
| 9004-64-2 | Cellulose, 2-hydroxypropyl ether |
| 9004-65-3 | Cellulose, 2-hydroxypropyl methyl ester |
| 9004-67-5 | Cellulose, methyl ether |
| 9005-25-8 | Cornstarch |
| 9005-38-3 | Sodium alginate |
| 9006-04-6 | Rubber |
| 9007-48-1 | 1,2,3-Propanetriol, homopolymer (9Z)-9-octadecenoate |
| 9009-32-9 | 1,2,3-Propanetriol, homopolymer, octadecanoate |
| 9050-36-6 | Maltodextrin |
| 994-36-5 | Citric acid, sodium salt |
| 10034-76-1 | Calcium sulfate, hemihydrate |
| 10034-99-8 | Magnesium sulfate heptahydrate |
| 10101-41-4 | Calcium sulfate, dihydrate |
| 10279-57-9 | Silica, hydrate |
| 11099-07-3 | Octadecanoic acid, ester with 1,2,3-propanetriol (9CI) |
| 11138-66-2 | Xanthan gum |
| 12001-26-2 | Mica group minerals |
| 12001-27-3 | Lime (chemical) dolomitic |
| 12003-38-2 | Mica |
| 12003-51-9 | Silicic acid ($H_4SiO_4$), aluminum sodium salt (1:1:1) |
| 12063-19-3 | Zinc iron oxide |
| 12068-86-9 | Iron magnesium oxide ($Fe_2MgO_4$) |
| 12168-85-3 | Calcium oxide silicate $Ca_3O(SiO_4)$) |
| 12207-97-5 | Magnesium oxide silicate ($Mg_3O(Si_2O_5)_2$), monohydrate |
| 12259-21-1 | Iron oxide ($Fe_2O_3$), hydrate |
| 12694-22-3 | 9-Octadecanoic acid, monoester with oxybis (propanediol) |
| 12736-96-8 | Silicic acid, aluminum potassium sodium salt |
| 13397-24-5 | Gypsum |
| 13397-26-7 | Carbonic acid, calcium salt (calcite) |
| 13429-27-1 | Tetradecanoic acid, potassium salt |
| 13776-74-4 | Silicic acid ($H_2SiO_3$), magnesium salt (1:1) |
| 13983-17-0 | Wollastonite |
| 14987-04-3 | Magnesium silicon oxide ($Mg_2Si_3O_8$) |
| 16389-88-1 | Dolomite ($CaMg(CO_3)_2$) |
| 18996-35-5 | Citric acid, monosodium salt |
| 24634-61-5 | Potassium sorbate |
| 25496-72-4 | 9-Octadecanoic acid (9Z)-, monoester with 1,2,3-propanetriol |
| 25637-84-7 | 9-Octadecenoic acid (9Z)-, diester with 1,2,3-propanetriol |
| 26402-22-2 | Decanoic acid, monoester with 1,2,3-propanetriol |
| 26402-26-6 | Octanoic acid, monoester with 1,2,3-propanetriol |
| 26499-65-0 | Plaster of Paris |
| 26657-95-4 | Hexadecanoic acid, diester with 1,2,3-propanetriol (9CI) |
| 26657-96-5 | Hexadecanoic acid, monoester with 1,2,3-propanetriol (9CI) |
| 27214-38-6 | Tetradecanoic acid, monoester with 1,2,3-propanetriol (9CI) |
| 27215-38-9 | Dodecanoic acid, monoester with 1,2,3-propanetriol (9CI) |
| 27638-00-2 | Dodecanoic acid, diester with 1,2,3-propanetriol (9CI) |
| 31566-31-1 | Octodecanoic acid, monoester with 1,2,3-propanetriol (9CI) |

APPENDIX A-continued

U.S. Environmental Protection Agency
List of Inert Pesticide Ingredients

| CAS # | Name |
|---|---|
| 36354-80-0 | Octodecanoic acid, diester with 1,2,3-propanetriol (9Cl) |
| 37244-96-5 | Nepheline syenite |
| 49553-76-6 | 9-Octodecanoic acid, ester with 1,2,3-propanetriol (9Cl) |
| 51395-75-6 | Cellulose, mixt. with cellulose carboxymethyl ether sodium salt |
| 53563-63-6 | Tetradecanoic acid, diester with 1,2,3-propanetriol (9Cl) |
| 53988-07-1 | Decanoic acid, diester with 1,2,3-propanetriol (9Cl) |
| 60676-86-0 | Silica, vitreous |
| 61789-97-7 | Tallow |
| 61789-98-8 | Cork |
| 61789-99-9 | Lard |
| 61790-53-2 | Diatomaceous earth (less than 1% crystalline silica) |
| 63231-67-4 | Silica Gel (Ca$_3$O(SiO$_4$))(Ca(SiO$_3$)) |
| 64044-51-5 | Lactose, monohydrate |
| 65996-61-4 | Cellulose, pulp |
| 68131-04-4 | Humic acid, sodium salt |
| 68131-12-4 | Meat meal |
| 68131-37-3 | Corn syrup solids |
| 68334-00-9 | Hydrogenated cottonseed oil |
| 68409-75-6 | Bone meal |
| 68424-10-2 | Cottonseed meal |
| 68442-85-3 | Cellulose, regenerated |
| 68476-25-5 | Feldspar group minerals (no asbestos and less than 1% crystalline silica) |
| 68476-37-9 | Glue (as depolymerized animal collagen) |
| 68476-78-8 | Cane syrup |
| 68514-28-3 | Humic acid, potassium salt |
| 68514-74-9 | Hydrogenated palm oils |
| 68514-76-1 | Citrus pulp, orange |
| 68525-86-0 | Corn flour |
| 68553-81-1 | Rice bran oil |
| 68876-77-7 | Yeast |
| 68916-18-7 | Coffee grounds |
| 68916-91-6 | Licorice extract |
| 68917-73-7 | Oils, wheat |
| 68917-75-9 | Wintergreen oil |
| 68937-99-5 | Sunflower seeds |
| 68989-22-0 | Zeolites, NaA |
| 68991-42-4 | Paprika |
| 71010-52-1 | Gellan gum (tolerance pending approval) |
| 71012-10-7 | 9-Octadecenoic acid, monoester with tetraglycerol |
| 84681-71-0 | Hydrogenated rapeseed oil |
| 85409-30-5 | Bentonite, sodian |
| 93763-70-3 | Perlite, expanded |
| 112926-00-8 | Silica gel, pptd., cryst.-free |
| 112945-52-5 | Silica, amorphous, fumed, cryst.-free |
| 120962-03-0 | Canola oil |
| 130885-09-5 | Perlite (no asbestos and less than 1% crystalline silica) |
| 134134-87-5 | Oat protein |
| — | Animal feed items conforming to 40 CFR 180.950(b) |
| — | Animal glue |
| — | Cardboard |
| — | Cat food |
| — | Clam shells |
| — | Commonly consumed food commodities conforming to 40 CFR 180.950(a) |
| — | Cotton |
| — | Douglas fir bark |
| — | Edible fats and oils conforming to 40 CFR 180.950(c) |
| — | Egg shells |
| — | Oyster shells |
| — | Paper |
| — | Peat moss |
| — | Sawdust |
| — | Vinegar (maximum of 8% acetic acid in solution) |

List B

| CAS # | Name |
|---|---|
| 50-21-5 | Lactic acid |
| 57-48-7 | D-Fructose |
| 57-55-6 | Propylene glycol |
| 57-88-5 | (3.beta.)-Cholest-5-en-3-ol |
| 58-08-2 | 1H-Purine-2,6-dione, 3,7-dihydro-1,3,7-trimethyl- |
| 58-56-0 | Thiamine mononitrate |
| 58-86-6 | D-Xylose |
| 59-30-3 | Folic acid |
| 60-00-4 | Ethylenediaminetetraacetic acid (EDTA) |
| 62-33-9 | Ethylenediaminetetraacetic acid (EDTA), calcium disodium |
| 63-68-3 | L-Methionine |
| 64-02-8 | Ethylenediaminetetraacetic acid (EDTA), tetrasodium salt |
| 64-17-5 | Ethanol |
| 64-19-7 | Acetic acid |
| 65-85-0 | Benzoic acid |
| 67-48-1 | Choline chloride |
| 67-63-0 | Isopropyl alcohol |
| 67-97-0 | Vitamin D3 |
| 68-19-9 | Vitamin B12 |
| 68-26-8 | Vitamin A |
| 71-23-8 | n-Propanol |
| 71-36-3 | 1-Butanol |
| 73-22-3 | L-Tryptophan |
| 77-90-7 | Acetyl tributyl citrate |
| 78-23-9 | Pentaerythritol monostearate |
| 79-09-4 | Propionic acid |
| 80-56-8 | alpha-Pinene |
| 81-88-9 | Rhodamine B (conforming to 40 CFR 180.2020) |
| 91-53-2 | Ethoxyquin |
| 94-13-3 | Propyl p-hydroxybenzoate |
| 96-48-0 | gamma-Butyrolactone |
| 97-78-9 | Glycine, N-methyl-N-(1-oxododecyl) |
| 98-86-2 | Acetophenone |
| 99-76-3 | Methyl p-hydroxybenzoate |
| 102-76-1 | Glyceryl triacetate |
| 103-26-4 | Methyl cinnamate |
| 106-65-0 | Butanedioic acid, dimethyl ester |
| 106-97-8 | n-Butane |
| 108-24-7 | Acetic anhydride |
| 110-15-6 | Butanedioic acid |
| 110-44-1 | Sorbic acid |
| 111-20-6 | Decanedioic acid |
| 111-27-3 | 1-Hexanol |
| 111-70-6 | 1-Heptanol |
| 112-30-1 | 1-Decanol |
| 112-62-9 | Methyl oleate |
| 115-10-6 | Dimethyl ether |
| 115-83-3 | Pentaerythritol tetrastearate |
| 120-72-9 | Indole, 1H- |
| 124-07-2 | Octanoic acid |
| 124-10-7 | Methyl tetradecanoate |
| 126-96-5 | Sodium diacetate |
| 134-03-2 | Sodium ascorbate |
| 137-08-6 | beta-Alanine,N-(2,4-dihydroxy-3,3-dimethyl-1-oxobutyl)-, calcium salt (2:1), (R)-(9CI) (CA IN |
| 137-40-6 | Sodium propionate |
| 139-33-3 | Ethylenediaminetetraacetic acid (EDTA), disodium salt |
| 139-44-6 | Glyceryl tris(12-hydroxystearate) |
| 141-78-6 | Ethyl acetate |
| 142-03-0 | Aluminum acetate, basic |

APPENDIX A-continued

U.S. Environmental Protection Agency
List of Inert Pesticide Ingredients

| CAS # | Name |
|---|---|
| 142-48-3 | Glycine, N-methyl-N-(1-oxooctadecyl) |
| 143-28-2 | Oleyl alcohol |
| 147-14-8 | Copper phthalocyanine blue |
| 147-81-9 | Arabinose (8CI, 9CI) |
| 150-38-9 | Ethylenediaminetetraacetic acid (EDTA), trisodium salt |
| 151-21-3 | Dodecyl sulfate, sodium salt |
| 334-48-5 | Capric acid |
| 497-19-8 | Sodium carbonate |
| 506-87-6 | Carbonic acid, diammonium salt |
| 515-98-0 | Ammonium lactate |
| 527-07-1 | Gluconic acid, sodium salt |
| 527-09-3 | Cupric gluconate |
| 533-96-0 | Sodium sesquicarbonate |
| 544-60-5 | Ammonium oleate |
| 563-71-3 | Ferrous carbonate |
| 577-11-7 | Sodium bis(2-ethylhexyl) sulfosuccinate |
| 584-08-7 | Carbonic acid, dipotassium salt |
| 598-62-9 | Carbonic acid, manganese(2+) salt (1:1) |
| 631-61-8 | Ammonium acetate |
| 637-12-7 | Aluminum stearate |
| 689-82-7 | 2-Butenedioic acid (Z)-, monopotassium salt |
| 811-97-2 | 1,1,1,2-Tetrafluoroethane |
| 814-80-2 | Calcium lactate |
| 860-22-0 | FD&C Blue No. 2 |
| 868-18-8 | Sodium tartrate |
| 928-96-1 | 3-Hexen-1-ol, (Z)- |
| 1066-33-7 | Ammonium bicarbonate |
| 1302-42-7 | Sodium aluminate |
| 1305-62-0 | Calcium hydroxide |
| 1305-78-8 | Calcium oxide |
| 1309-42-8 | Magnesium hydroxide |
| 1310-58-3 | Potassium hydroxide |
| 1310-73-2 | Sodium hydroxide |
| 1312-76-1 | Potassium silicate |
| 1317-95-9 | Tripoli |
| 1318-23-6 | Boehmite (Al(OH)O) |
| 1328-53-6 | C.I. Pigment Green 7 |
| 1336-21-6 | Ammonium hydroxide |
| 1338-41-6 | Sorbitan monostearate |
| 1343-98-2 | Silicic acid |
| 1344-09-8 | Sodium silicate |
| 1344-28-1 | Aluminum oxide |
| 1344-43-0 | Manganous oxide |
| 1639-66-3 | Sodium dioctyl sulfosuccinate |
| 2809-21-4 | 1-Hydroxyethylidene-1,1-diphosphonic acid |
| 3012-65-5 | Ammonium citrate, dibasic |
| 3624-77-9 | Glycine, N-methyl-N-(1-oxo-9-octadecenyl)-, sodium salt (9CI) (CA INDEX NAME) |
| 4075-81-4 | Calcium propionate |
| 4468-02-4 | D-Gluconic acid, zinc complex |
| 5136-55-0 | Glycine, N-methyl-N-(1-oxooctadecyl)-, sodium salt |
| 5905-52-2 | Ferrous lactate |
| 5964-35-2 | Ethylenediaminetetraacetic acid (EDTA), tetrapotassium salt |
| 5989-27-5 | d-Limonene |
| 6028-57-5 | Aluminum octanoate |
| 6381-92-6 | Ethylenediaminetetraacetic acid (EDTA), disodium salt dihy |
| 6107-56-8 | Calcium octanoate |
| 6484-52-2 | Ammonium nitrate |
| 6834-92-0 | Silicic acid (H2SiO3), disodium salt |
| 7320-34-5 | Tetrapotassium pyrophosphate |
| 7379-28-3 | Ethylenediaminetetraacetic acid (EDTA), potassium salt |
| 7379-28-4 | Ethylenediaminetetraacetic acid (EDTA), sodium salt |
| 7439-89-6 | Iron (Fe) |
| 7440-59-7 | Helium |
| 7440-66-6 | Zinc (metallic) |
| 7446-70-0 | Aluminum chloride |
| 7558-79-4 | Disodium phosphate |
| 7558-80-7 | Sodium dihydrogen phosphate |
| 7601-54-9 | Trisodium phosphate |
| 7631-99-4 | Sodium nitrate |
| 7632-05-5 | Sodium phosphate |
| 7647-01-0 | Hydrogen chloride |
| 7647-15-6 | Sodium bromide |
| 7664-38-2 | Phosphoric acid |
| 7664-93-9 | Sulfuric acid |
| 7681-38-1 | Sodium bisulfate |
| 7681-49-4 | Sodium fluoride |
| 7681-53-0 | Sodium hypophosphite |
| 7697-37-2 | Nitric acid |
| 7705-08-0 | Ferric chloride |
| 7720-78-7 | Ferrous sulfate |
| 7722-76-1 | Ammonium phosphate (monobasic) |
| 7722-88-5 | Diphosphoric acid, tetrasodium salt |
| 7727-43-7 | Barium sulfate (1:1) |
| 7722-88-5 | Tetrasodium pyrophosphate |
| 7757-86-0 | Phosphoric acid, magnesium salt (1:1) |
| 7757-87-1 | Phosphoric acid, magnesium salt (2:3) |
| 7757-93-9 | Phosphoric acid, calcium salt (1:1) |
| 7758-11-4 | Potassium phosphate (dibasic) |
| 7758-16-9 | Sodium acid pyrophosphate |
| 7758-23-8 | Phosphoric acid, calcium salt (2:1) |
| 7758-29-4 | Sodium tripolyphosphate |
| 7758-87-4 | Tricalcium phosphate |
| 7772-98-7 | Sodium thiosulfate |
| 7778-53-2 | Phosphoric acid, tripotassium salt |
| 7778-77-0 | Potassium phosphate, monobasic |
| 7779-88-6 | Zinc nitrate |
| 7779-90-0 | Phosphoric acid, zinc salt (2:3) |
| 7782-44-7 | Oxygen |
| 7782-63-0 | Ferrous sulfate heptahydrate |
| 7783-20-2 | Ammonium sulfate |
| 7783-28-0 | Diammonium phosphate |
| 7784-25-0 | Ammonium alum |
| 7785-87-7 | Manganese sulfate |
| 7785-88-0 | Sodium aluminum phosphate |
| 7786-30-3 | Magnesium chloride |
| 7803-63-6 | Ammonium bisulfate |
| 8000-25-7 | Oils, rosemary |
| 8000-46-2 | Oils, geranium |
| 8001-26-1 | Linseed oil (boiled) |
| 8001-69-2 | Cod liver oil |
| 8002-09-3 | Pine oil |
| 8002-33-3 | Sulfated castor oil |
| 8002-72-0 | Onions, oil |
| 8005-44-5 | Fatty alcohols |
| 8007-08-7 | Oils, ginger |
| 8008-57-9 | Orange oil |
| 8008-79-5 | Spearmint oil |
| 8009-03-8 | Petrolatum |
| 8014-19-5 | Oils, palmarosa |
| 8015-73-4 | Oils, basil |
| 8016-20-4 | Oils, grapefruit |
| 8016-85-1 | Oils, tangerine |
| 8016-96-4 | Oils, vetiver |
| 8021-28-1 | Oils, Fir |
| 8021-99-6 | Charcoal, bone |
| 8022-15-9 | Oils, lavandin |
| 8022-56-8 | Oils, sage |
| 8023-77-6 | Resins, oleo-, capsicum |
| 8023-84-5 | Catnip |
| 8028-48-6 | Sweet orange peel tincture |
| 8028-89-5 | Caramel |
| 8029-31-0 | Beer |
| 8030-12-4 | Tallow, |
| 8050-33-7 | Polyoxyethylene ester of rosin |

APPENDIX A-continued

U.S. Environmental Protection Agency
List of Inert Pesticide Ingredients

| CAS # | Name |
|---|---|
| 8052-48-0 | Sodium tallow soap |
| 8061-51-6 | Lignosulfonic acid, sodium salt |
| 8061-52-7 | Lignosulfonic acid, calcium salt |
| 9000-01-5 | Gum Arabic |
| 9000-50-4 | Oils, oakmoss-resinoid (CA INDEX NAME) |
| 9000-69-5 | Pectin |
| 9000-70-8 | Gelatin |
| 9000-71-9 | Casein |
| 9002-86-2 | Polyvinyl chloride resin |
| 9002-89-5 | Polyvinyl alcohol |
| 9002-92-0 | Polyoxyethylene dodecyl mono ether |
| 9003-01-4 | Acrylic acid polymer |
| 9003-04-7 | Acrylic acid polymer, sodium salt |
| 9003-05-8 | Polyacrylamide |
| 9003-06-9 | Acrylamide - acrylic acid resin |
| 9003-07-0 | Polypropylene |
| 9003-09-2 | Ethene, methoxy-, homopolymer |
| 9003-11-6 | Polyoxyethylene-polyoxypropylene copolymer |
| 9003-18-3 | Acrylonitrile—butadiene copolymer |
| 9003-18-3 | 2-Propenenitrile, polymer with 1,3-butadiene |
| 9003-20-7 | Polyvinyl acetate |
| 9003-22-9 | Vinyl chloride - vinyl acetate copolymer |
| 9003-39-8 | Polyvinylpyrrolidone |
| 9003-49-0 | Polymerized butyl acrylate |
| 9003-53-6 | Polystyrene resin |
| 9003-55-8 | Butadiene-styrene copolymer |
| 9003-56-9 | 2-Propenenitrile, polymer with 1,3-butadiene and ethenylbenzene |
| 9003-68-3 | Polyethylene terephthalate |
| 9003-70-7 | Styrene-divinyl benzene copolymer resin matrix |
| 9004-81-3 | Polyoxyethylene monolaurate |
| 9004-82-4 | Dodecanol, ethoxylated, monoether with sulfuric acid, sodium salt |
| 9004-95-9 | Polyoxyethylene monohexadecyl ether |
| 9004-96-0 | Polyoxyethylene monooleate |
| 9004-98-2 | Polyoxyethylene mono(cis-9-octadecenyl) ether |
| 9004-99-3 | Polyoxyethylene monostearate |
| 9005-00-9 | Polyoxyethylene monooctadecyl ether |
| 9005-07-6 | Polyoxyethylene dioleate |
| 9005-08-7 | Polyoxyethylene distearate |
| 9005-37-2 | Propylene glycol alginate |
| 9005-42-9 | Ammonium caseinate |
| 9005-46-3 | Sodium caseinate |
| 9005-64-5 | Polyoxyethylene sorbitan monolaurate |
| 9005-65-6 | Polyoxyethylene sorbitan monooleate |
| 9005-66-7 | Polyoxyethylene sorbitan monopalmitate |
| 9005-67-8 | Polyoxyethylene sorbitan monostearate |
| 9005-70-3 | Polyoxyethylene sorbitan trioleate |
| 9005-71-4 | Polyoxyethylene sorbitan tristearate |
| 9006-50-2 | Egg white |
| 9011-05-6 | Urea-formaldehyde resin |
| 9011-13-6 | Styrene - maleic anhydride resin |
| 9011-14-7 | Polymethyl methacrylate |
| 9011-16-9 | Maleic anhydride - methylvinyl ether copolymer |
| 9011-29-4 | Polyoxyethylene sorbitol hexastearate |
| 9012-76-4 | Chitosan |
| 9014-85-1 | Polyethylene glycol ether with 1,4-diisobutyl-1,4-dimethylbutynediol (2:1) |
| 9014-90-8 | Nonylphenol, ethoxylated, monoether with sulfuric acid, sodium salt |
| 9014-92-0 | Polyoxyethylene dodecylphenol |
| 9014-93-1 | Polyoxyethylene dinonylphenol |
| 9016-45-9 | Polyoxyethylene nonylphenol |
| 9018-04-6 | 1,4-Butanediol, copolymer with 4,4'-diphenylmethane diisocyanate and polytetramethylene glycol |
| 9033-79-8 | 2-Propenoic acid, polymer with sodium 2-propenoate |
| 9036-19-5 | Polyoxyethylene (1,1,3,3-tetramethylbutyl)phenyl ether |
| 9038-29-3 | Oxirane, methyl-, polymer with oxirane, decyl ether |
| 9038-95-3 | Polyethylene-polypropylene glycol, monobutyl ether |
| 9041-33-2 | Oxirane, methyl-, polymer with oxirane, mono-2-propenyl ether |
| 9063-38-1 | Starch, carboxymethyl ether, sodium salt |
| 9064-13-5 | Poly[oxy(methyl-1,2-ethanediyl)], alpha(methylphenyl)-omega-hydroxy |
| 9081-17-8 | Nonylphenol, ethoxylated, monoether with sulfuric acid |
| 9084-06-4 | Naphthalenesulfonic acid, polymer with formaldehyde, sodium salt |
| 10016-20-3 | alpha—Cyclodextrin |
| 10025-67-9 | Sulfur chloride |
| 10028-22-5 | Ferric sulfate |
| 10043-01-3 | Aluminum sulfate |
| 10043-52-4 | Calcium chloride |
| 10102-17-7 | Sodium thiosulfate, pentahydrate |
| 10103-46-5 | Calcium phosphate |
| 10124-56-8 | Sodium hexametaphosphate |
| 10191-41-0 | 2H-1-Benzopyran-6-ol,3,4-dihydro-2,5,7,8-tetramethyl-2-(4,8,12-trimethyltridecyl)- |
| 10213-79-3 | Silicic acid, disodium salt, pentahydrate |
| 10361-29-2 | Carbonic acid, ammonium salt |
| 10377-60-3 | Magnesium nitrate |
| 12001-76-2 | Vitamin B complex |
| 12124-97-9 | Ammonium bromide |
| 12125-02-9 | Ammonium chloride |
| 12173-47-6 | Hectorite |
| 12174-11-7 | Attapulgite |
| 12269-78-2 | Pyrophyllite |
| 12276-01-6 | Ethylenediaminetetraacetic acid (EDTA), copper (II) salt |
| 13092-66-5 | Phosphoric acid, magnesium salt (2:1) |
| 13463-67-7 | Titanium dioxide |
| 13870-28-5 | Silicic acid ($H_2Si_2O_5$), disodium salt |
| 14025-15-1 | Ethylenediaminetetraacetic acid (EDTA), disodium copper salt |
| 14025-21-9 | Ethylenediaminetetraacetic acid (EDTA), disodium zinc salt |
| 14464-46-1 | Cristobalite |
| 14729-89-6 | Ethylenediaminetetraacetic acid (EDTA) disodium iron (II) salt |
| 14807-96-6 | Talc (no asbestos and less than 1% crystalline silica) |
| 14977-37-8 | Potassium magnesium sulfate ($Mg_2K_2(SO_4)_3$) |
| 15375-84-5 | Ethylenediaminetetraacetic acid (EDTA) disodium manganese |
| 15468-32-3 | Tridymite ($SiO_2$) |
| 15593-82-5 | Silicic acid ($H_6Si_2O_7$), hexasodium salt |
| 15708-41-5 | Ethylenediaminetetraacetic acid (EDTA) iron(III) sodium salt |

APPENDIX A-continued

U.S. Environmental Protection Agency
List of Inert Pesticide Ingredients

| CAS # | Name |
|---|---|
| 15974-07-9 | Calcium zinc phosphate ($CaZn_2(PO_4)_2$) |
| 17099-81-9 | Ethylenediaminetetraacetic acid (EDTA), iron(III) salt |
| 17217-76-4 | 1,2,3-Propanetricarboxylic acid, 2-hydroxy-, iron (3+) salt (1:1), trihydrate |
| 17421-79-3 | Ethylenediaminetetraacetic acid (EDTA) monosodium salt |
| 17572-97-3 | Ethylenediaminetetraacetic acid (EDTA), tripotassium salt |
| 18917-93-6 | Magnesium lactate |
| 19019-43-3 | Glycine, N-(carboxymethyl)-N-[2[(carboxymethyl)amino]ethyl]-, trisodium salt |
| 21645-51-2 | Aluminum hydroxide |
| 20344-49-4 | Iron hydroxide oxide (Fe(OH)O) |
| 20427-59-2 | Copper (II) hydroxide |
| 20727-33-7 | Dioctyl* sodium sulfosuccinate-methylheptyl) (* octyl is 1-methylheptyl) |
| 20824-56-0 | Ethylenediaminetetraacetic acid (EDTA), diammonium salt |
| 21645-51-2 | Aluminum hydroxide |
| 21662-09-9 | 4-Decenal, (4Z)- |
| 24937-78-8 | Ethylene, polymer witrh vinyl acetate |
| 24937-78-8 | Ethylene, polymer with vinyl acetate |
| 24938-04-3 | Polyethylene terphthalate-polyethylene isophthalate film |
| | Propenoic acid, 2-methyl-butyl ester, polyer with 2-(dimethylamino)ethyl 2-methyl-2-propenoate and methyl 2- |
| 24938-16-7 | 2-methyl-2-propenoate |
| 24968-79-4 | Acrylic acid methyl ester, polymer with acrylonitrile |
| 25038-59-9 | Poly(ethylene terephthalate) |
| 25067-01-0 | Vinyl acetate, polymer with n-butyl acrylate |
| 25085-02-3 | Sodium acrylate, polymer with acrylamide |
| 25085-34-1 | Styrene acrylic acid copolymer |
| 25085-39-6 | 2-Propenoic acid, polymer with 1,3-butadiene and ethenylbenzene |
| 25085-41-0 | Vinyl acetate-butyl acrylate-acrylic acid terpolymer |
| 25086-29-7 | Vinylpyrrolidinone-styrene polymer |
| 25086-48-0 | Vinyl chloride, vinyl acetate and vinyl alcohol copolymer |
| 25086-89-9 | Polyvinylpyrrolidone-vinyl acetate copolymer |
| 25087-06-3 | Maleic acid monoethyl ester-vinyl methyl ether copolymer |
| 25119-68-0 | Maleic acid monobutyl ester-vinyl methyl ether copolymer |
| 25119-83-9 | Acrylic acid, copolymer with butyl acrylate |
| 25135-39-1 | Acrylic acid, polymer with ethyl acrylate and methylmethacrylate |
| 25153-40-6 | Methyl vinyl ether-maleic acid copolymer |
| 25212-88-8 | Ethyl acrylate-methacrylic acid copolymer |
| 25213-02-9 | 1-Hexene, polymer with ethene |
| 25213-24-5 | Vinyl alcohol-vinyl acetate copolymer |
| 25231-21-4 | Polyoxypropylene monostearyl ether |
| 25266-02-8 | Maleic anhydride-1-octadecene copolymer |
| 25322-68-3 | Polyethylene glycol |
| 25322-69-4 | Polypropylene glycol |

APPENDIX A-continued

U.S. Environmental Protection Agency
List of Inert Pesticide Ingredients

| CAS # | Name |
|---|---|
| 25608-12-2 | 2-Propenoic acid, homopolymer, potassium salt |
| 25719-52-2 | Dodecyl 2-methylacrylate polymer |
| 25719-60-2 | beta-Pinene homopolymer |
| 25750-06-5 | Styrene-methyl methacrylate-2-ethylhexyl acrylate copolymer |
| 25750-84-9 | Acrylic acid, butyl ester, polymer with ethylene |
| 25956-17-6 | FD&C Red No. 40 |
| 25987-30-8 | Acrylic acid, polymer with acrylamide, sodium salt |
| 25987-66-0 | Acrylic acid butyl ester, polymer with methacrylic acid, methyl methacrylate and styrene |
| 26027-38-3 | p-Nonylphenol, ethoxylated |
| 26099-09-2 | Maleic acid homopolymer |
| 26160-96-3 | Butylated polyvinylpyrrolidone |
| 26183-44-8 | Dodecyl alcohol, ethoxylated, monoether with sulfuric acid |
| 26183-52-8 | Polyoxyethylene monodecyl ether |
| 26266-57-9 | Sorbitan monohexadecanoate |
| 26316-40-5 | Ethylene oxide-propylene oxide copolymer ethylenediamine ether |
| 26337-35-9 | Acetic acid ethenyl ester, polymer with carbon monoxide and ethene |
| 26604-01-3 | Acrylic acid, polymer with acrylonitrile, ethyl acrylate and N-(hydroxymethyl)acrylamide |
| 26635-76-7 | Glycols, polyethylene, mono(oleylamines)-ethyl ester |
| 26636-39-5 | Polyoxyethylene monoeicosyl ether |
| 26636-40-8 | Polyoxyethylene docosyl ether |
| 26873-77-8 | 2-Propenoic acid, 2-methyl-, polymer with ethenylbenzene, 2-ethylhexyl 2-propenoate and 2-propene |
| 26915-70-8 | Tridecanol, ethoxylated, phospate ester |
| 27012-62-0 | Acrylic acid methyl ester, polymer with acrylonitrile and 1,3-butadiene |
| 27252-80-8 | Poly(oxy-1,2-ethanediyl), alpha-methyl-omega(2-propenyloxy)-(CA INDEX NAME) |
| 27274-31-3 | Poly(oxy-1,2-ethanediyl),.alpha.-2-propenyl-.omega.-hydroxy- |
| 27306-78-1 | Poly(oxy-1,2-ethanediyl), alpha-methyl-omega[3-[1,3,3,3-tetramethyl-1-[(trimethylsilyl)oxy]disiloxanyl]propoxy]-(2-propenyloxy) |
| 27306-79-2 | Polyoxyethylene monotetradecyl ether |
| 27458-93-1 | Isooctadecanol |
| 27756-15-6 | Acrylic acid-stearyl methacrylate copolymer |
| 27937-16-4 | Poly[imino(1-oxo-1,12-dodecanediyl)] |
| 28062-44-4 | Vinyl pyrrolidone-acrylic acid copolymer |
| 28211-18-9 | 2-Pyrrolidinone, 1-ethenyl-, polymer with 1-eicosene |
| 28430-58-2 | Vinyl acetate, polymer with methyl acrylate and methyl methacrylate |
| 29437-34-1 | 2-Propenoic acid, butyl ester, polymer with ethyl 2-propenoate and 2-propenenitrile |
| 29710-31-4 | Cetyl octanoate |
| 29781-80-4 | (alpha-D-Glucopyranoside, octyl |
| 29836-26-8 | (beta-D-Glucoopyranoside, octyl |
| 30364-51-3 | Glycine, N-methyl-N-(1-oxotetradecyl)-, sodium salt |
| 30581-59-0 | Vinyl pyrrolidone-dimethylaminoethylmethacrylate copolymer |

APPENDIX A-continued

U.S. Environmental Protection Agency
List of Inert Pesticide Ingredients

| CAS # | Name |
|---|---|
| 30795-23-4 | 2-Propenoic acid, butyl ester, polymer with ethenylbenzene and 2-ethylhexyl 2-propenoate |
| 30938-41-1 | Polymer of vinyl acetate, n-butyl acrylate, vinyl chloride, and acrylic acid |
| 31307-92-3 | Polyoxyethylene sorbitol |
| 31307-95-6 | Maleic acid monoisopropyl ester-vinyl methyl ether copolymer |
| 31394-71-5 | Polypropylene glycol monooleate |
| 31800-88-1 | Octyloxypoly(ethyleneoxy)ethyl phosphate |
| 32649-30-2 | 2-Butenedioic acid (Z)-, polymer with ethenol, sodium salt |
| 36347-52-1 | Ethanaminium, N,N,N-trimethyl-2-[(2-methyl-1oxo-2-propenyl)oxy]-, chloride, polymer with methyl 2-methyl-2-propenoate |
| 36653-82-4 | Cetyl alcohol |
| 37199-81-8 | Maleic anhydride, polymer with 2,4,4-trimethylpentene, sodium salt |
| 37280-82-3 | Polyoxyethylene polyoxypropylene phosphate |
| 37286-64-9 | Polyoxypropylene monomethyl ether |
| 37340-60-6 | Nonylphenol, ethoxylated, phosphate ester, sodium salt |
| 37764-25-3 | N,N-Diallyl-2,3-dichloroacetamide |
| 39362-51-1 | Oxirane, methyl-, polymer with oxirane, acetate |
| 39464-64-7 | Dinonylphenol, ethoxylated, phosphated |
| 41444-50-2 | Octyl glucoside |
| 41444-55-7 | Decyl glucoside |
| 41487-53-0 | 2-Propenoic acid, 2-methyl-, polymer with ethyl 2-propenoate, sodium salt |
| 41928-09-0 | Polyethylene glycol ether with 2,2' methylenebis(4-(tert-octyl)phenol) (2:1) |
| 50769-39-6 | Butylpolyethoxyethanol esters of phosphoric acid 4B |
| 51192-09-7 | Polyoxyethylene glycerin monooleate |
| 51609-41-7 | 4-Nonylphenol, ethoxylated, phosphate ester |
| 51617-79-9 | Polyoxyethylene octadecylphenol |
| 51811-79-1 | Nonylphenol, ethoxylated, phosphate ester |
| 52503-15-8 | Polyethylene glycol nonylphenyl ether phosphate potassium salt |
| 52558-73-3 | Glycine, N-methyl-N-(1-oxotetradecyl) |
| 52831-04-6 | Acrylic acid-alpha-methylstyrene-styrene copolymer |
| 53504-41-9 | Polyurethane |
| 54116-08-4 | Sodium tridecylpoly(oxyethylene) sulfate |
| 54549-23-4 | D-Glucoside, octyl |
| 55069-68-6 | Polyethylene glycol hexaether with sorbitol, diester with dodecanoic and oleic acids |
| 55989-05-4 | 2-Propenoic acid, 2-methyl-, polymer with ethyl 2-propenoate and methyl 2-methyl-2-propenoate, ammonium salt |
| 56090-69-8 | Oxirane, methyl-, polymer with oxirane, monoacetate, 2-propenyl ether |
| 56388-96-6 | Poly(oxyethylene)tridecylacetic acid |
| 57171-56-9 | Polyoxyethylene sorbitol hexaoleate |
| 57451-03-3 | Nonylphenol, ethoxylated, monoether with sulfuric acid, triethanolamine salt |
| 58128-22-6 | Octadecanoic acid, 12-hydroxy-, homopolymer, octadecanoate |
| 58846-77-8 | N-Decyl glucoside |
| 59139-23-0 | Polyethylene glycol nonylphenyl ether phosphate ethanolamine salt |
| 59766-31-3 | Potassium titanium oxide ($K_2Ti_8O_{17}$) |
| 59800-21-4 | Poly(oxy-1,2-ethanediyl), alpha-hydro-omegahydroxy-, ether with D-glucitol (6:1),-9-octadecenoate |
| 59947-99-8 | beta-D-Glucoside, decyl |
| 60092-15-1 | Maleic anhydride-methylstyrene copolymer, sodium salt |
| 60828-78-6 | Polyoxyethylene 2,6,8-trimethyl-4-nonyl ether |
| 60864-33-7 | Benzyl ether of 1,1,3,3-tetramethylbutylphenoxy polyethoxy ethanol |
| 60874-89-7 | Polyethylene glycol ether with methylenebis(diamylphenol) |
| 61725-89-1 | Oxirane methyl-, polymer with oxirane, tridecyl ether |
| 61788-60-1 | Methyl esters of cottonseed oil |
| 61789-14-8 | Glycerides, tallow sesqui-, hydrogenated |
| 61789-30-8 | Potassium coconut oil soap |
| 61790-37-2 | Fatty acids, tallow |
| 61790-38-3 | Fatty acids, tallow, hydrogenated |
| 61790-90-7 | Fatty acids, tall-oil, hexaester with sorbitol, ethoxylated |
| 61790-92-9 | Fatty acids, tall-oil, pentaester with sorbitol, ethoxylated |
| 61791-12-6 | Castor oil, ethoxylated |
| 61791-23-9 | Soybean oil, ethoxylated |
| 61791-26-2 | Amines, tallow alkyl, ethoxylated |
| 61791-31-9 | N,N-Bis(2-hydroxyethyl)(coconut oil alkyl)amine |
| 61824-34-8 | Polyoxyethylene sorbitol pentaoleate |
| 61827-84-7 | Oxirane, methyl-, polymer with oxirane, octyl ether |
| 61016-40-3 | Ethylenediaminetetraacetic acid (EDTA) disodium copper (II) |
| 62386-95-2 | Methyl vinyl ether-maleic acid copolymer calcium sodium salt |
| 63089-86-1 | Polyoxyethylene sorbitol tetraoleate |
| 63148-62-9 | Silicones and siloxanes, dimethyl |
| 63150-03-8 | 2-Propenoic acid, 2-methyl-, dodecyl ester, polymer with eicosyl 2-methyl-2-propenoate, hexadecyl 2-methyl-2-propenoate, octadecyl 2-methyl-2-propenoate, pentadecyl 2-methyl-2-propenoate, tetradecyl 2-methyl-2-propenoate and tridecyl 2-methyl-2-propenoate |
| 63231-81-2 | Poly(vinylpyrrolidone-1-hexadecene) |
| 63393-89-5 | Coumarone-indene resin |
| 63428-83-1 | Polyamide resins |
| 63705-03-3 | Polyglycerol diisostearate |
| 63744-68-3 | Butyl acrylate-ethyl acrylate-methacrylic acid-methyl methacrylate-styrene copolymer |
| 63798-35-6 | Starch acetate adipate |
| 64754-90-1 | Chlorinated polyethylene |
| 65405-40-5 | Butyl acrylate-vinyl acetate-acrylic acid copolymer |
| 65996-63-6 | Starch, acid-hydrolyzed |
| 65997-15-1 | Cement, portland, chemicals |
| 66070-75-5 | Fatty acids, tall-oil, polymers with bisphenol A and epichlorohydrin |

APPENDIX A-continued

U.S. Environmental Protection Agency
List of Inert Pesticide Ingredients

| CAS # | Name |
|---|---|
| 66070-87-9 | Polyglyceryl phthalate ester of coconut oil fatty acid |
| 66071-03-2 | Linseed oil, polymd., oxidized |
| 66071-16-7 | Soybean oil, polymer with maleic anhydride |
| 66071-94-1 | Corn, steep liquor |
| 66402-68-4 | Metakaolin |
| 67401-50-7 | Ethylenediaminetetraacetic acid (EDTA), tetrasodium salt |
| 67674-67-3 | Poly(oxy-1,2-ethanediyl), .alpha.-3-[1,3,3-tetramethyl-1[(trimethylsilyl)oxy]disiloxanyl]propyl]-omega.hydroxy- |
| 67701-08-0 | Fatty acids, $C_{16-18}$ and $C_{18}$-unsatd |
| 67701-09-1 | Potassium salts of fatty acids (C8-18 and C18 unsatd.) |
| 67701-10-4 | Soap: (Fatty acids, C8-18 and C18-unsatd., sodium salts) |
| 67746-08-1 | Linseed oil, polymd. |
| 67761-98-2 | Fatty acids, tall-oil, polymer with ethylene glycol, pentaerythritol, and phthalic anhydride |
| 67762-09-8 | Soybean oil, polymer with ethylene glycol, glycerol, pentaerythritol and phthalic anhydride |
| 67762-38-3 | Fatty acids, $C_{16-18}$ & $C_{18}$-unsatd., Me esters |
| 67762-87-2 | Siloxanes and silicones, di-Me, 3-hydroxypropyl Me, ethers with polyethylene-polypropylene glycol |
| 67762-90-7 | Dimethyl silicone polymer with silica |
| 67762-96-3 | Siloxanes and silicones, di-Me, hydroxyterminated, ethers with polypropylene glycol mono-Bu ether |
| 67922-57-0 | Polyethylene glycol nonylphenyl ether phosphate magnesium salt |
| 68002-20-0 | 1,3,5-Triazine-2,4,6-triamine, polymer with formaldehyde, methylated |
| 68002-70-0 | Glycerides, $C_{16-22}$ |
| 68037-40-1 | 2,5-Furandione, polymer with ethylbenzene, sulfonated, sodium salt |
| 68037-62-7 | Siloxanes and silicones, di-Me, Me hydrogen, reaction products with polyethylene glycol monoacetate |
| 68038-31-3 | Fatty acids, tall-oil, polymers with pentaerythritol, phthalic anhydride and rosin |
| 68071-54-5 | Castor oil, dehydrated, polymer with p-tertbutylbenzoic acid, glycerol and phthalic anhydride (CA INDEX NAME) |
| 68130-47-2 | Poly(oxy-1,2-ethanediyl), alpha-hydro-omega-hydroxy-mono-$C_{8-10}$-alkyl ethers, phosphates |
| 68131-29-3 | Soybean oil, polymer with phthalic anhydride, trimellitic anhydride and trimethylolpropane |
| 68131-40-8 | Alcohols, $C_{11}$-$C_{15}$-secondary, ethoxylated |
| 68152-57-8 | Rosin, fumarated, polymer with ethylene glycol and pentaerythritol |
| 68153-10-6 | Oils, lard, sulfated, sodium salts, |
| 68154-33-6 | Fatty acids, coco, esters with sorbitan, ethoxylated- |
| 68187-71-3 | Calcium salts of tall-oil fatty acids |
| 68187-76-8 | Castor oil, sulfated, sodium salt |
| 68187-84-8 | Castor oil, oxidized |
| 68201-51-4 | Oils, menhaden, oxidized |
| 68308-36-1 | Soybean meal |
| 68309-49-9 | Soybean oil, polymer with isophthalic acid, linseed oil and trimethylolpropane |
| 68333-69-7 | Rosin, maleated, polymer with pentaerythritol |
| 68333-79-9 | Ammonium polyphosphate |
| 68411-97-2 | Glycine, N-methyl-, N-coco acyl derivs. INDEX NAME) |
| 68413-17-2 | Fatty acids, tall-oil, polymers with isophthalic acid, pentaerythritol and walnut oil |
| 68424-50-0 | Fatty acids, tall-oil, $C_{12-15}$-alkyl esters, sulfated, sodium salts |
| 68424-61-3 | Glycerides, $C_{16-18}$ and $C_{18}$-unsatd. mono- and di- |
| 68425-44-5 | Amides, coco, N-(hydroxyethyl), ethoxylated |
| 68440-66-4 | Siloxanes and silicones, di-Me, 3-hydroxypropyl Me, ethers with polypropylene glycol mono-Bu ether (CA INDEX NAME) (Pending) |
| 68441-17-8 | Oxidized polyethylene |
| 68458-49-1 | Polyphosphoric acids, esters with polyethylene glycol nonylphenyl ether |
| 68476-82-4 | Peanut meal |
| 68511-11-5 | Hexanedioic acid, polymer with 1,4-butanediol and 1,2-propanediol, didodecanoate |
| 68513-95-1 | Soy flour |
| 68514-61-4 | Milk, hydrolyzed |
| 68514-75-0 | Oils, orange-juice |
| 68525-90-6 | Fatty acids, $C_{8-18}$, esters with sorbitol, ethoxylated |
| 8526-94-3 | Alcohols, $C_{12-20}$ |
| 68527-08-2 | Alkenes, C > 10 .alpha.-, polymd. |
| 68551-13-3 | Alcohols, $C_{12-15}$, ethoxylated propoxylated |
| 68553-02-6 | Fatty acids, coco, esters with polyethylene glycol ether with glycerol (3:1) |
| 68554-64-3 | Siloxanes and silicones, di-Me, 3-hydroxypropyl Me, ethers with polyethylene glycol mono-Me ether |
| 68585-15-9 | Oxirane, methyl, polymer with oxirane, mono $C_6$-$C_{10}$ alkyl ethers, phosphates |
| 68601-19-5 | Poly(oxy-1,2-ethanediyl), .alpha.,.alpha.'[[methyl[3-(tridecyloxy)propyl]imino]di-2,1 ethanediyl |
| 68605-57-2 | Fatty acids, tall-oil, polymers with bisphenol A, epichlorohydrin, rosin and tung oil |
| 68608-58-2 | Whey |
| 68611-44-9 | Silane, dichlorodimethyl-, reaction products with silica |
| 68630-83-1 | Styrene, polymer with methacrylic acid and polyethoxylated (Z)-2-butenedioic acid |
| 68646-20-4 | Sorbitol tall oil fatty acid sesquiester, ethoxylated |
| 68648-20-4 | Fatty acids, tall-oil, sesquiesters with sorbitol, ethoxylated |
| 68648-89-5 | Benzene, ethenyl-, polymer with 2-methyl-1,3-butadiene, ydrogenated |
| 68650-09-9 | Fatty acids, tall-oil, mixed esters with glycerol and polyethylene glycol |
| 68650-28-2 | Polyethylene glycol-polyisobutenyl anhydride-tall oil fatty acid copolymer |

APPENDIX A-continued

U.S. Environmental Protection Agency
List of Inert Pesticide Ingredients

| CAS # | Name |
|---|---|
| 68890-80-2 | Benzene, ethenyl-, polymer with 2,5-furandione, 2-butoxyethyl ester, ammonium salt |
| 68891-29-2 | Alcohols, $C_{8-10}$, ethoxylated, monoether with sulfuric acid, ammonium salt |
| 68908-64-5 | Poly(oxy-1,2-ethanediyl), -hydro-. omega.-hydroxy-, mono-$C_{10-12}$-alkyl ethers, phosphates |
| 68909-20-6 | Silanamine, 1,1,1-trimethyl-N-(trimethylsilyl)-, hydrolysis products with silica |
| 68917-18-0 | Cornmint oil |
| 68919-53-9 | Fatty acids, soya, Me esters |
| 68919-54-0 | Sunflower-oil fatty acids, Me ester |
| 68920-66-1 | Alcohols, $C_{16-18}$ and $C_{18}$-unsatd., ethoxylated |
| 68920-69-4 | Alcohols, $C_{9-11}$, propoxylated |
| 68937-55-3 | Siloxanes and silicones, di-Me, 3-hydroxypropyl Me, ethoxylated propoxylated |
| 68938-54-5 | Siloxanes and silicones, di-Me, 3-hydroxypropyl Me, ethers with polyethylene glycol mono-Me ether |
| 69011-22-9 | Benzene, diethenyl-, polymer with etenylbenzene and ethenylethylbenzene, sulfonated, sodium salts |
| 69227-21-0 | Alcohols, $C_{12-18}$, ethoxylated propoxylated |
| 69364-63-2 | Poly(oxy-1,2-ethanediyl), alpha-isohexadecylomega-hydroxy- |
| 69669-25-6 | Potassium salts of fatty acids-$C_{20}$) |
| 70131-50-9 | Clay |
| 70142-34-6 | 12-Hydroxystearic acid-polyethylene glycol copolymer |
| 70425-89-7 | Isooctyl acrylate-stearyl methacrylate-acrylic acid copolymer |
| 70549-17-6 | Butyl acrylate-2-ethylhexyl acrylate-2-hydroxyethyl acrylate-styrene copolymer |
| 70632-06-3 | Alcohols, $C_{12-15}$, ethoxylated, carboxylated, sodium salts |
| 71012-10-7 | Oleic acid, 2-(2-(2-(2 hydroxyethoxy)ethoxy) ethoxy)ethyl ester |
| 71394-17-7 | 2-Propenoic acid, 2-methyl-, polymer with butyl 2-methyl-2-propenoate, ethenylbenzene, 2-ethylhexyl 2-propenoate and methyl 2--methyl-2-propenoate |
| 71526-07-3 | 1-Oxa-4-azaspiro[4.5]decane, 4-(dichloroacetyl) |
| 71820-36-5 | Castor oil, maleic anhydride, and polyethylene glycol copolymer |
| 72869-69-3 | Oils, apricot |
| 73038-25-2 | Poly(oxy-1,2-ethanediyl), alpha-isotridecylomega-hydroxy-, phosphate |
| 73050-07-4 | Poly(oxy-1,2-ethanediyl),.alpha.(butoxyhydroxyphosphinyl)-.omega.-hydroxy,$C_{13-15}$-alkyl ethers, sodium salts |
| 73050-08-5 | Poly(oxy-1,2-ethanediyl), .alpha.,.alpha.'phosphinicobis [.omega.-hydroxy-, di-$C_{13-15}$-alkyl ethers, sodium salts |
| 73050-09-6 | Poly(oxy-1,2-ethanediyl),.alpha.-phosphono.omega.-hydroxy-,$C_{13-15}$-alkyl ethers, disodium salts |
| 73513-47-0 | Ethylenediaminetetraacetic acid (EDTA) disodium zinc salt, dih |
| 73637-19-1 | Ethylenediaminetetraacetic acid (EDTA) disodium copper(II) salt |
| 73637-20-4 | Ethylenediaminetetraacetic acid (EDTA) disodium manganese |
| 73891-99-3 | Rape oil, |
| 74504-64-6 | 1,2,3-Propanetriol, homopolymer, dodecanoate |
| 74775-06-7 | Poly[oxy(methyl-1,2-ethanediyl)],.alpha.-(1 oxopropyl)-.omega.-(tetradecyloxy)- |
| 74811-65-7 | Croscarmellose sodium |
| 78266-09-8 | 1-Propanesulfonic acid, 2-hydroxy-3-(2-propenyloxy)-,monosodium salt, polymer with 2-propenoic acid |
| 78330-24-2 | Poly(oxy-1,2-ethanediyl),.alpha.-hydro-.omega.hydroxy-, mono-$C_{11-14}$-isoalkyl ethers, $C_{13}$-rich, phosphates |
| 84775-78-0 | Ascophyllum nodosum, ext |
| 85637-75-8 | Oxirane, methyl-, polymer with oxirane, mono[2-(2-butoxyethoxy) ethyl] ether |
| 86864-96-2 | 2-Propenoic acid, polymer with 2-hydroxypropyl 2-propenoate and sodium 2-propenoate |
| 87823-33-4 | 3,5-Bis(6-isocyanatohexyl)-2H-1,3,5-oxadiazine-2,4,6-(3H,5H)-trione, polymer with diethylenetriamine |
| 89511-79-5 | 2-Propenoic acid, 2-methyl-.polymer with ethyl 2-propenoate and methyl 2-methyl-2-propenoate, sodium salt |
| 89678-90-0 | Acrylic acid, styrene, .alpha.-methyl styrene copolymer, ammonium salt |
| 91994-94-4 | Acetylated lanolin alcohol |
| 97043-91-9 | Alcohols, $C_{9-16}$, ethoxylated |
| 97675-81-5 | Fish meal |
| 97676-23-8 | Licorice extract (licorice and licorice derivates) |
| 97765-70-3 | Cheese |
| 97766-30-8 | Orange, sweet, valencia, ext. |
| 97953-25-8 | Acrylic acid-sodium acrylate-sodium-2-methylpropanesulfonate copolymer |
| 99607-70-2 | Acetic acid, [(5-chloro-8-quinolinyl)oxy]-, 1-methylhexyl ester (9CI) |
| 99734-09-5 | Polyethylene glycol mono(tristyrylphenyl)ether |
| 100403-38-1 | Glycerides, animal, reaction products with sucrose |
| 100403-39-2 | Glycerides, palm-oil, reaction products with sucrose |
| 100403-40-5 | Glycerides, tallow, reaction products with sucrose |
| 100403-41-6 | Glycerides, vegetable-oil, reaction products with sucrose |
| 100934-04-1 | Methacrylic acid-methyl methacrylate-polyethylene glycol methyl ether methacrylate copolymer |
| 102900-02-7 | Poly(oxyethylene/oxypropylene) monoalkyl($C_6$-$C_{10}$)ether sodium fumarate adduct |
| 104133-09-7 | Tetraethoxysilane, polymer with hexamethyldisiloxane |
| 105362-40-1 | Triethanolamine, compd. with poly(oxyethylene) tristyrylphenyl ether phosphate |

APPENDIX A-continued

U.S. Environmental Protection Agency
List of Inert Pesticide Ingredients

| CAS # | Name |
|---|---|
| 108419-34-7 | Acetic acid, $C_{9-11}$-branched alkyl esters, $C_{10}$-rich |
| 109961-42-4 | 2-Propenenitrile, polymer with 1,2,4-triethenylcyclohexane, hydrolyzed |
| 114033-68-0 | 2-Propenoic acid, polymer with 2-propanol, reaction products with sodium acrylate |
| 114133-44-7 | Hexanedioic acid, polymer with N-(2-aminoethyl)1,3-propanediamine, aziridine, (chloromethyl)oxirane, 1,2-ethanediamine, N,N"-1,2-ethanediylbis[1,3-propanediamine], formic acid and .alpha.-hydro.omega.-hydroxypoly(oxy,2-ethanediyl) |
| 117272-76-1 | Siloxanes and silicones, 3-hydroxypropyl Me, ethers with polyethylene glycol mono-Me ether |
| 119432-41-6 | Poly(oxy-1,2-ethanediyl), .alpha.-sulfo-.omega.[tris(1-phenylethyl)phenoxy]-ammonium salt |
| 119724-54-8 | Methyl methacrylate-methacrylic acid monomethoxypolyethylene glycol methacrylate copolymer |
| 121776-33-8 | 3-(Dichloroacetyl)-5-(2-furanyl)-2,2dimethyloxazolidine |
| 125303-89-1 | Castor oil, hydrogenated, polymer with adipic acid, ethylenediamine and 12-hydroxyoctadecanoic acid |
| 125826-44-0 | Hexanedioic acid, polymer with 2,2-dimethyl-1,3-propanediol,-hexanediol, hydrazine, 3-hydroxy-2-(hydroxymethyl)-2-methylpropanoic acid and 1,1'-methylenebis[4-isocyanatocyclohexane], compd. with N,N-diethylethanamine |
| 125997-17-3 | Poly(oxy-1,2-ethanediyl),.alpha.-acetyl-.omega.-[3-{1,3,3,3-tetramethyl-1[(trimethylsilyl) oxy]disiloxanyl]propoxy)- |
| 127036-24-2 | Poly(oxy-1,2-ethanediyl),.alpha.-undecyl.omega.-hydroxy-, branched and linear |
| 128446-33-3 | 1-alpha-Cyclodextrin, 2-hydroxypropyl ethers |
| 128497-20-1 | Oils, Macadamia |
| 130353-60-5 | Acrylic acid-divinyl benzene copolymer |
| 130498-22-5 | Wheat flour |
| 132175-04-3 | Polyethylene glycol-polyisobutenyl anhydride-tall oil fatty acid copolymer |
| 132538-94-4 | Oils, orange-juice, citrus sinensis |
| 132580-45-1 | Alpha[2,4,6-Tris[1-(phenyl)ethyl}phenyl]-omega hydroxypoly(oxyethylene) poly(oxypropylene) copolymer |
| 134180-76-0 | Oxirane, methyl-, polymer with oxirane, mono[3-[1,3,3,3-tetramethyl-1[(trimethylsilyl)oxy]disiloxanyl] propyl] ether |
| 135590-91-9 | Diethyl-1-(2,4-dichlorophenyl)-5-methyl-2-pyrazolin-3,5-dicarboxylate |
| 137091-12-4 | Acetic acid ethenyl ester, polymer with ethanol and alpha-2-propenyl-omega-hydroxypoly(oxy-1,2-ethandiyl) |
| 139871-83-3 | 2-Butenedioic acid (Z)_, polymer with ethenol and ethenyl acetate, sodium salt |
| 143819-63-0 | Poly(oxy-1,2-ethanediyl), .alpha.-hydro-.omega.hydroxy-, monoether with (hydroxymethyl)decane |
| 151006-66-5 | Acrylic acid terpolymer, partial sodium salt |
| 154518-36-2 | Alcohols, $C_{9-11}$-iso-, $C_{10}$-rich, ethoxylated propoxylated |
| 162627-18-1 | Fatty acids, $C_{18}$-unsatd., trimers, reaction products with triethylenetetramine |
| 163436-84-8 | Polyoxyethylene tristyrylphenol phosphate, potassium salt |
| 163520-33-0 | 3-Isoxazolecarboxylic acid, 4,5-dihydro-5,5-diphenyl-, ethyl ester |
| 176022-82-5 | Poly[oxy(methyl-1,2-ethanediyl)],.alpha.-[2-[bis(2 hydroxyethyl)amino]propyl]-.omega.-hydroxy-, ether with.alpha.-hydro-.omega. hydroxypoly(oxy-1,2-ethanediyl) (1:2), mono-$C_{12-16}$-alkyl ethers |
| 188027-78-3 | 5H-1,3-Dioxolo[4,5-f]benzimidazole, 6-chloro-5-[(3,5 dimethyl-4-isoxazolyl)sulfonyl]-2,2-difluoro |
| 374602-90-1 | Ashes (residues), sunflower seed hull |
| — | Crustacea (raw and processed forms) |
| — | Dried crickets |
| — | Dried mealworms |
| — | Eggs (raw and processed forms) |
| — | Fish (raw and processed forms) |
| — | Ground grass seed |
| — | Leaves, apple |
| — | Milk (raw and processed forms) |
| — | Nitrogen fixing bacteria |
| — | Peanut shells |
| — | Peanuts (raw and processed forms) |
| — | Pecan shell flour |
| — | Polymer of n-butyl acrylate, methyl methacryalate, methacrylic acid and aminopropyl methacrylate |
| — | Sand |
| — | Seeds, lettuce |
| — | Silkworm pupae |
| — | Soybeans (raw and processed forms) |
| — | Sulfur Coated Urea |
| — | Thumb tacks |
| — | Tree nuts (raw and processed forms) |
| — | Wood flower |
| — | Wheat (raw and processed forms) |

What is claimed is:

1. A method suitable in organic production for killing, controlling or suppressing a plant, comprising:

providing a liquid herbicidal composition comprising a herbicidally active limonene component, polyoxyethoxylated castor oil, octyphenol ethoxylate, potassium carbonate, and castor oil and spraying said herbicidal composition onto one or more leaves of a plant.

2. The method according to claim 1, wherein said liquid herbicidal composition additionally comprises an added oil component, wherein said added oil component is a natural product obtained by non-chemical means and/or is an inert pesticide ingredient contained in the Environmental Protection Agency's List 4A or 4B.

3. The method according to claim 1 wherein said spraying comprises spraying in a manner whereby the herbicidal composition contacts at least 60% of the surface area of the plant's leaf or leaves.

4. The method of according to claim 1, wherein said providing includes providing a liquid herbicidal composition having said herbicidal limonene component present in said composition at a concentration of from about 10% to about 20%.

5. The method according to claim 2, wherein said providing includes providing a liquid herbicidal composition having an added oil component present at a concentration of from about 0.5% to about 6%.

6. The method according to claim 5, wherein said liquid herbicidal composition includes an added oil component selected from the group consisting of cottonseed oil, soybean oil, sunflower oil, pine oil, coconut oil and combinations thereof.

7. The method according to claim 6, wherein said liquid herbicidal composition includes an emulsifying agent, wherein said emulsifying agent is selected from the group consisting of ethoxylated nonylphenol, alkylether mono & di-phosphate ester, 2,6,8-trimethyl-4-nonyl ether ethoxylate, poly(oxy-1,2-ethanediyl), alpha-(nonylphenyl-omega-hydroxy), and combinations thereof.

8. The method according to claim 5, wherein said providing includes providing a composition containing poly(oxy-1,2-ethanediyl), and alpha-(nonylphenyl-omega-hydroxy-).

9. A method for non-selective burn down of plants compatible with organic production, the method comprising:
(a) selecting an area having at least one plant growing therein; and
(b) spraying a liquid herbicide composition onto said area, said herbicide composition comprising a herbicidally active limonene component, polyoxyethoxylated castor oil, octyphenol ethoxylate, potassium carbonate, and castor oil.

10. The method according to claim 9, wherein said spraying includes spraying said liquid herbicide composition containing an added oil component.

11. The method according to claim 10, wherein said spraying includes spraying said liquid herbicide composition containing from about 0.5% to about 6% of said added oil component.

12. The method according to claim 11, wherein said spraying includes spraying said liquid herbicide composition containing an added oil component selected from the group consisting of cottonseed oil, soybean oil, sunflower oil, pine oil, coconut oil and a combination thereof.

13. The method according to claim 12, wherein said spraying includes spraying said liquid herbicide composition containing emulsifying agents selected from the group consisting of nonylphenol polyoxyethylene 10 phosphate ester, alkylether mono & di-phosphate ester; 2,6,8-trimethyl-4-nonyl ether ethoxylate; poly(oxy-1,2-ethanediyl), alpha-(nonylphenyl-omega-hydroxy); and combinations thereof.

14. The method according to claim 13, wherein said spraying includes spraying said liquid herbicide composition containing poly(oxy-1,2-ethanediyl), and alpha-(nonylphenyl-omega-hydroxy).

15. The method according to claim 9, wherein said spraying includes spraying said liquid herbicide composition containing a wetting agent.

16. The method according to claim 15, wherein said spraying includes spraying said liquid herbicide composition containing a wetting agent selected from the group consisting of nonylphenol ethoxylate, dodecyl sulfate, sodium salt, caseins and combinations thereof.

17. A herbicidal composition for use in organic production, comprising a herbicidally active limonene component, polyoxyethoxylated castor oil, octyphenol ethoxylate, potassium carbonate, and castor oil.

18. The herbicidal composition according to claim 17, and further comprising an added oil component, wherein said added oil component is a natural product obtained by non-chemical means and/or is an inert pesticide ingredient contained in the Environmental Protection Agency's List 4A or 4B.

19. The herbicidal composition according to claim 18, wherein said limonene component is present at a concentration from about 2% to about 25%.

20. The herbicidal composition according to claim 18, containing from about 0.5% to about 6% of said added oil component.

21. The herbicidal composition according to claim 20, wherein said added oil component is selected from the group consisting of cottonseed oil, soybean oil, sunflower oil, pine oil, coconut oil and combinations thereof.

22. The herbicidal composition according to claim 21, wherein said herbicidal composition includes an emulsifying agent selected from the group consisting of nonylphenol polyoxyethylene 10 phosphate ester; alkylether mono & di-phosphate ester; 2,6,8-trimethyl-4-nonyl ether ethoxylate; poly(oxy-1,2-ethanediyl), alpha-(nonylphenyl-omega-hydroxy); and combinations thereof.

23. The herbicidal composition according to claim 22, wherein said emulsifying agent comprises at least one surfactant and said composition contains from about 0.5% to about 15% of said at least one surfactant.

24. The herbicidal composition according to claim 23, wherein said at least one surfactant includes poly(oxy-1,2-ethanediyl), and alpha-(nonylphenyl-omega-hydroxy).

25. A ready-to-use composition according to claim 17 wherein the composition further comprises an inert pesticide ingredient included in the Environmental Protection Agency's List 4A or 4B.

26. A herbicidal concentrate adapted to be diluted with water and used in organic production, the herbicidal concentrate comprising a herbicidally active limonene component, polyoxyethoxylated castor oil, octyphenol ethoxylate, potassium carbonate, and castor oil.

27. The herbicidal concentrate according to claim 26, and further comprising a member selected from the group consisting of a wetting agent, a pH modifier effective to provide a pH greater than 5, an added oil component, and combinations thereof, wherein said member selected is a natural product obtained by non-chemical means and/or is an inert pesticide ingredient contained in the Environmental Protection Agency's List 4A or 4B.

28. The herbicidal concentrate according to claim 27, having an added oil component selected from the group consisting of cottonseed oil, soybean oil, sunflower oil, pine oil, coconut oil and combinations thereof.

29. The herbicidal concentrate according to claim 27, having an emulsifying agent comprising at least one surfactant selected from the group consisting of nonylphenol polyoxyethylene 10 phosphate ester, alkylether mono & di-phosphate ester; 2,6,8-trimethyl-4-nonyl ether ethoxylate; poly(oxy-1,2-ethanediyl), alpha-(nonylphenyl-omega-hydroxy); and combinations thereof.

30. The herbicidal concentrate according to claim 29, having an added oil component at a concentration of from about 4% to about 12%.

31. The herbicidal concentrate according to claim 30, wherein said emulsifying agent comprises poly(oxy-1,2-ethanediyl), and alpha-(nonylphenyl-omega-hydroxy).

32. The herbicidal concentrate of claim 31, wherein said limonene comprises from about 8% to about 85% of said concentrate.

33. A concentrate according to claim 26 wherein the concentrate further comprises an inert pesticide ingredient included in the Environmental Protection Agency's List 4A or 4B.

34. A method for making a herbicide composition, comprising:
    (a) providing a liquid herbicide formulation comprising a herbicidally active limonene component, polyoxyethoxylated castor oil, octyphenol ethoxylate, potassium carbonate, and castor oil, and
    (b) diluting and mixing said formulation with water.

35. The method according to claim 34, wherein said liquid herbicide formulation includes an added oil component selected from the group consisting of cottonseed oil, soybean oil, sunflower oil, pine oil, coconut oil and combinations thereof.

36. The method according to claim 35, wherein said liquid formulation includes an emulsifying agent which comprises at least one surfactant selected from the group consisting of nonylphenol polyoxyethylene 10 phosphate ester; alkylether mono & di-phosphate ester; 2,6,8-trimethyl-4-nonyl ether ethoxylate; poly(oxy-1,2-ethanediyl), alpha-(nonylphenyl-omega-hydroxy); and combinations thereof.

37. The method according to claim 36, wherein said liquid herbicide formulation includes limonene at a concentration of from about 35% to about 85%.

38. The method according to claim 37, wherein said liquid herbicide formulation includes an added oil component at a concentration of from about 2% to about 20%.

39. The method according to claim 37, wherein said liquid herbicide formulation includes an emulsifying agent at a concentration of from about 5% to about 20%.

40. A kit for providing a ready-to-use herbicide composition suitable for organic production comprising:
    a container having therein a ready-to-use liquid herbicide composition, the herbicide comprising a herbicidally active limonene component, polyoxyethoxylated castor oil, octyphenol ethoxylate, potassium carbonate, and castor oil; and
    instructions, recorded in a medium, for applying the herbicide composition to a pre-selected area for indiscriminately killing, controlling or suppressing plants growing in the area.

41. The kit according to claim 40, wherein said liquid herbicide composition contains a limonene component at a concentration of from about 2% to about 25%, an emulsifying agent at a concentration of from about 0.05% to about 15%, and an added oil component at a concentration of from about 0.5% to about 6%.

42. The kit according to claim 41, wherein:
    (a) said emulsifying agent comprises at least one surfactant selected from the group consisting of nonylphenol polyoxyethylene 10 phosphate ester; alkylether mono & di-phosphate ester; 2,6,8-trimethyl-4-nonyl ether ethoxylate; poly(oxy-1,2-ethanediyl), alpha-(nonylphenyl-omega-hydroxy); and combinations thereof, and
    (b) said added oil component is selected from the group consisting of cottonseed oil, soybean oil, sunflower oil, pine oil, coconut oil and combinations thereof.

43. The kit according to claim 42, wherein said surfactants include poly(oxy-1,2-ethanediyl), and alpha-(nonylphenyl-omega-hydroxy).

44. The kit of claim 40, further including a label stating "for organic production."

45. A kit for providing a herbicide composition suitable for use in organic production comprising:
    a container having therein a liquid herbicide concentrate, the herbicide concentrate comprising a herbicidally active limonene component, polyoxyethoxylated castor oil, octyphenol ethoxylate, potassium carbonate, and castor oil; and
    instructions, recorded in a medium, for diluting the concentrate with water to provide a herbicide composition.

46. The kit according to claim 45, wherein said liquid herbicide concentrate contains a limonene component at a concentration of from about 35% to about 85%, an emulsifying agent at a concentration of from about 1% to about 30%, and an added oil component at a concentration of from about 2% to about 20%.

47. The kit according to claim 46, wherein:
    (a) said emulsifying agent comprises at least one surfactant selected from the group consisting of nonylphenol polyoxyethylene 10 phosphate ester; alkylether mono & di-phosphate ester; 2,6,8-trimethyl-4-nonyl ether ethoxylate; poly(oxy-1,2-ethanediyl), alpha-(nonylphenyl-omega-hydroxy); and combinations thereof, and
    (b) said added oil component is selected from the group consisting of cottonseed oil, soybean oil, sunflower oil, pine oil, coconut oil and combinations thereof.

48. The kit according to claim 47, wherein said surfactants include poly(oxy-1,2-ethanediyl), and alpha-(nonylphenyl-omega-hydroxy).

49. The kit of claim 43, further including a label stating "for organic production."

* * * * *